(12) United States Patent
Bothe et al.

(10) Patent No.: US 9,487,554 B2
(45) Date of Patent: Nov. 8, 2016

(54) ESTRA-1,3,5(10),16-TETRAENE-3-CARBOXAMIDE DERIVATIVES, PROCESSES FOR THEIR PREPARATION, PHARMACEUTICAL PREPARATIONS COMPRISING THEM AND THEIR USE FOR PREPARING MEDICAMENTS

(71) Applicants: BAYER INTELLECTUAL PROPERTY GmbH, Monheim (DE); BAYER PHARMA AKTIENGESELLSCHAFT, Berlin (DE)

(72) Inventors: Ulrich Bothe, Berlin (DE); Naomi Barak, Berlin (DE); Matthias Busemann, Berlin (DE); Oliver Martin Fischer, Berlin (DE); Andrea Rotgeri, Berlin (DE); Isabella Gashaw, Berlin (DE); Ingo Hartung, Berlin (DE); Tobias Marquardt, Berlin (DE)

(73) Assignees: Bayer Intellectual Property GmbH (DE); Bayer Pharma Aktiengesellschaft (DE)

( * ) Notice: Subject to any disclaimer, the term of this patent is extended or adjusted under 35 U.S.C. 154(b) by 103 days.

(21) Appl. No.: 14/348,645

(22) PCT Filed: Sep. 24, 2012

(86) PCT No.: PCT/EP2012/068803
§ 371 (c)(1),
(2) Date: Mar. 31, 2014

(87) PCT Pub. No.: WO2013/045407
PCT Pub. Date: Apr. 4, 2013

(65) Prior Publication Data
US 2014/0249119 A1    Sep. 4, 2014

(30) Foreign Application Priority Data

Sep. 29, 2011 (DE) .................. 10 2011 083 725

(51) Int. Cl.
*A61K 31/58* (2006.01)
*C07J 43/00* (2006.01)
*A61K 45/06* (2006.01)

(52) U.S. Cl.
CPC .............. *C07J 43/003* (2013.01); *A61K 31/58* (2013.01); *A61K 45/06* (2013.01)

(58) Field of Classification Search
CPC .............................. C07J 43/003; A61K 31/58
USPC .................... 540/2, 95, 96; 514/176
See application file for complete search history.

(56) References Cited

U.S. PATENT DOCUMENTS

| 5,604,213 A | 2/1997 | Barrie et al. |
| 6,541,463 B1 | 4/2003 | Labrie et al. |
| 2005/0203075 A1 | 9/2005 | Agoston et al. |

FOREIGN PATENT DOCUMENTS

| CL | 3883-08 | 11/2010 |
| WO | WO-2008065100 | 6/2008 |
| WO | WO-2009120565 | 10/2009 |
| WO | WO-2010091306 | 8/2010 |
| WO | WO-2011134954 | 11/2011 |

OTHER PUBLICATIONS

Azzarello, Joseph T, "Expression of AKR1C3 in renal cell carcinoma, papillary urothelial carcinoma, and Wilms' tumor", Int J Clin Exp Pathol, 3(2), (2010), 147-155.
Birtwistle, Jane, "The aldo-keto reductase AKR1C3 contributes to 7,12-dimethylbenz(a) anthracene-3,4-dihydrodiol mediated oxidative DNA damage in myeloid cells: Implications for leukemogenesis", Mutat Res, 662(1-2), (2009), 67-74.
Bydal, Patrick, "Steroidal lactones as inhibitors of 17β-hydroxysteroid dehydrogenase type 5: Chemical synthesis, enzyme inhibitory activity, and assessment of estrogenic and androgenic activities", Eur J of Med Chem, 44, (2009), 632-644.
Byrns, Michael C, "Aldo-keto reductase 1C3 expression in MCF-7 cells reveals roles in steroid hormone and prostglandin metabolism that may explain its over-expression in breast cancer", J Steroid Biochem Mol Biol, 118(3), (2010), 177-187.
Byrns, Michael C, "Inhibitors of type 5 17β-hydroxysteroid dehydrogenase (AKR1C3): Overview and structural insights", Journal Steroid Biochem Molecular Biology, 125, (2011), 95-104.
Colombe, Laurent, "Prostaglandin metabolism in human hair follicle", Exp Dermatol, 16(9), (2007), 762-769.
Czako, Barbara, "Discovery of Potent and Practical Antiangiogenic Agents Inspired by Cortistatin A", JACS, 131, (2009), 9014-9019.
Day, Joanna M, "Design and validation of specific inhibitors of 17β-hydroxysteroid dehydrogenases for therapeutic application in breast and prostate cancer, and in endometriosis", Endocrine-Related Cancer, 15, (2008), 665-692.
Deluca, Dominga, "Inhibitory effects of fluorine-substituted estrogens on the activity of 17beta-hydroxysteroid dehydrogenases", Mol. Cell Endocrinol, 248, (2006), 218-224.

(Continued)

*Primary Examiner* — Barbara P Badio
(74) *Attorney, Agent, or Firm* — Resek Liang & Frank, LLP; Stanley D. Liang

(57) ABSTRACT

The invention relates to AKR1C3 inhibitors and to processes for their preparation, to their use for the treatment and/or prophylaxis of diseases and also to their use for preparing medicaments for the treatment and/or prophylaxis of diseases, in particular bleeding disorders and endometriosis.

8 Claims, 1 Drawing Sheet

(56) References Cited

OTHER PUBLICATIONS

Delvoux, Bert, "Increased Production of 17β-Estradiol in Endometriosis Lesions Is the Result of Impaired Metabolism", Endocrinol Metab., 94, (2009), 876-883.

Descomps, Bernard, "Etude Du Site Actif De La 17β-Hydroxysteroide : NAD(P) Oxydoreductase Soluble Du Placenta Humain (•),", Bull. Soc. Chim. Biol. Bd., 51(12), S, (Jan. 1, 1970), 1591-1611.

Dufort, Isabelle, "Characteristics of a Highly Labile Human Type 5 17β-Hydroxysteroid Dehydrogenase", Endocrinology, 140, (1999), 568-574.

Ehmer, Peter B, "Development of a simpe and rapid assay for the evaluation of inhibitors of human 17α-hydroxylase-C 17,20-lyase (P450c17) by coexpression of P450c17 with NADPH-cytochrome-P450-reductase in *Escherichia coli*", J. Steroid Biochem. Mol. Biol., 75, (2000), 57-63.

Einspanier, A, "Induction of endometriosis in the marmoset monkey (Callithrix jacchus)", Mol Hum Reprod, (2006).

Figueroa, Jonine D, "Bladder cancer risk and genetic variation in AKR1C3 and other metabolizing genes", Carcinogenesis, 29(10), (2008), 1955-1962.

Fung, K-M, "Increased expression of type 2 3α-hydroxysteroid dehydrogenase/type 5 17β-hydroxysteroid dehydrogenase (AKR1C3) and its relationship with androgen receptor in prostate carcinoma", Endocr Relat Cancer, 13(1), (2006), 169-180.

Haidar, Samer, "Novel steroidal pyrimidyl infibitors of P450 17 (17α-hydroxylase/C17-20 lyase)", Archiv der Pharmizie, 334, 12, (2001), 373-374.

Halim, Marlin, "Imaging Induction of Cytoprotective Enzymes in Intact Human Cells: Coumberone, a Metabolic Reporter for Human AKR1C Enzymes Reveals Activation by Panaxytriol, an Active Component of Red Ginseng", J. Am. Chem. Soc., 130, (2008), 14123-14128.

Harnisch, Wolfram, "A Novel Approach to Cardenolides", J. Org. Chem., 50, (1985), 1990-1992.

He, Chunyan, "A large-scale candidate gene association study of age at menarche and age at natural menopause", Hum Genet, 125(5), (2010), 515-527.

Kerns, "Solubility Methods in: Drug-like Properties", Concepts, Structure Design and Methods, (2008), 276-286.

Knapp, David M, "A General Solution for Unstable Boronic Acids:Slow-Release Cross-Coupling from Air-Stable MIDA Boronates", J. Am. Chem. Soc., 131, (2009), 6961.

Lan, Qing, "Genetic polymorphisms in the oxidative stress pathway and susceptibility to non-Hodgkin lymphoma", Hum Genet, 121(2), (2007), 161-168.

Lan, Qing, "Oxidative damage-related genes AKR1C3 and 0GG1 modulate risks for lung cancer due to exposure to PAH-rich coal combustion emissions", Carcinogenesis, 25(11), (2004), 2177-2181.

Li, Pui Kai, "Estrone sulfate analogs as estrone sulfatase inhibitors", Steroids, 60, 3, (1995), 299-306.

Lovering, Andrew L, "Crystal Structures of Prostaglandin D2 11-Ketoreductase (AKR1C3) in Complex with the Nonsteroidal Anti-Inflammatory Drugs Flufenamic Acid and Indomethacin", Cancer Res, 64(5), (2004), 1802-1810.

Marchais-Oberwinkler, Sandrine, "17β-Hydroxysteroid dehydrogenases (17β-HSDs) as therapeutic targets: Protein structures, functions, and recent progress in inhibitor development", J Steroid Biochem Molecular Biol, 125, (2011), 66-82.

Messinger, Josef, "Estone C15 derivatives—A new class of 17β-Hydroxysteroid dehydrogenase type 1 inhibitors", Molecular Cellular Endocrinol, 301, (2009), 216-224.

Molander, Gary A, "Scope of the Suzuki—Miyaura Cross-Coupling Reactions of Potassium Heteroaryltrifluoroborates", J. Org. Chem., 74, (2009), 973.

Moreira, V M, "CYP17 Inhibitors for Preostate Cancer Treatment—An Update", Curr Med Chem., vol. 15, No. 9, (2008).

Ohlmann, C H, "Was kommt nach Docetaxel?", Urologe, 49, (2010), 64-68.

Oster, Alexander, "Bicyclic Substituted Hydroxyphenylmethanones as Novel Inhibitors of 17β-Hydroxysteroid Dehydrogenase Type 1 (17β-HSD1) for the Treatment of Estrogen-Dependent Diseases", J. Med. Chem., (2010), 8176-8186.

Penning, Trevor M, "Aldo-keto reductase (AKR) 1C3: Role in prostate disease and the development of specific inhibitors", Mol Cell Endocrinol, 248 (1-2), (2006), 182-191.

Penning, Trevor M, "Structure-function aspects and inhibitor desing of type 5 17β-hydroxysteroid dehydrogenase (AKR1C3)", Mol. Cell. Endocrinol. Bd., 171 (1-2), S, (Jan. 22, 2001), 137-149.

Pierrou, Stefan, "Expression of Genes Involved in Oxidative Stress Responses in Airway Epithelial Cells of Smokers with Chronic Obstructive Pulmonary Disease", Am J Respir Crit Care, 175(6), (2007), 577-586.

Potter, "Novel Steroidal Inhibitors of Human Cytochrome P45017α (17α-Hydroxylase-C17,20-lyase); Potential Agents for the Treatment of Prostatic Cancer", J. Med. Chem., 38, (1995), 2463-2471.

Qin, Kenan, "Identification of a Functional Polymorphism of the Human Type 5 17β-Hydroxysteroid Dehydrogenase Gene Associated with Polycystic Ovary Syndrome", J. Endocrinol Metab, 91(1), (2006), 270-276.

Rizner, Tea Lanisnik, "AKR1C1 and AKR1C3 may determine progesterone and estrogen ratios in endometrial cancer", Mol Cell Endocrinol, 248(1-2), (2006), 126-135.

Roberts, "Polymorphisms in Genes Involved in Sex Hormone Metabolism May Increase Risk of Benign Prostatic Hyperplasia", Prostate, 66(4), (2006), 392-404.

Smuc, Tina, "Disturbed estrogen and progesterone action in ovarian endometriosis", Mol Cell Endocrinol, 301 (1-2), (2009), 59-64.

Svensson, Per-Arne, "Regulation of Human Aldoketoreductase 1C3 (AKR1C3) Gene Expression in the Adipose Tissue", Cell Mol Biol Lett, 13(4), (2008), 599-613.

Yee, Dominic J, "Fluorogenic metabolic probes for direct activity readout of redox enzymes: Selective measurement of human AKR1C2 in living cells", Proc. Natl. Acad. Sci., 103, (2006), 13304-13309.

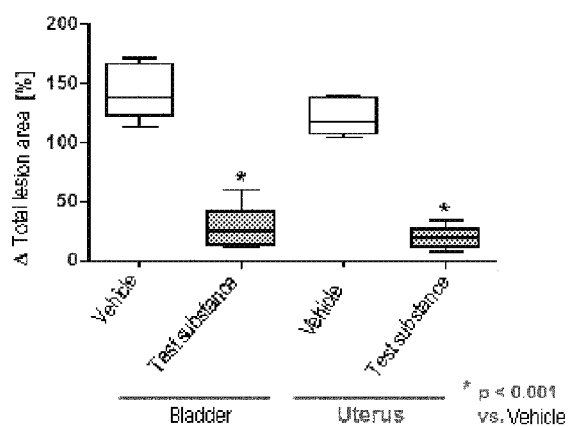
Difference of the lesion areas of the lesions located on the uterus or the bladder in per cent.

ESTRA-1,3,5(10),16-TETRAENE-3-CARBOXAMIDE DERIVATIVES, PROCESSES FOR THEIR PREPARATION, PHARMACEUTICAL PREPARATIONS COMPRISING THEM AND THEIR USE FOR PREPARING MEDICAMENTS

The invention relates to AKR1C3 inhibitors and to processes for their preparation, to their use for the treatment and/or prophylaxis of diseases and also to their use for preparing medicaments for the treatment and/or prophylaxis of diseases, in particular bleeding disorders and endometriosis.

AKR1C3 is a multifunctional enzyme and catalyses inter alia the reduction of 4-androstene-3,17-dione (a weak androgen) to testosterone (a potent androgen) and of oestrone (a weak oestrogen) to 17β-oestradiol (a strong oestrogen). In addition, the reduction of prostaglandin (PG) H2 to PGF2α and PGD2 to 9α,11β-PGF2 is inhibited (T. M. Penning et. al., 2006, 'Aldo-keto reductase (AKR) 1C3: Role in prostate disease and the development of specific inhibitors', Molecular and Cellular Endocrinology 248(1-2), 182-191).

The local formation of oestradiol (E2) plays a central role in the initiation and progression of breast cancer disorders and endometriosis. Reduction of the tissue concentrations of oestrogens and in particular of oestradiol is achieved by therapeutic administration of aromatase inhibitors (to inhibit the formation of oestrogens from androgens) and of sulphatase inhibitors (to block the formation of oestrone from oestrone sulphate). However, both therapeutic approaches have the disadvantage that systemic oestrogen concentrations are radically reduced (A. Oster et. al., J. Med. Chem. 2010, 53, 8176-8186). Recently, it has been demonstrated experimentally that endometriotic lesions are capable of synthesizing oestradiol locally (B. Delvoux et al., J Clin Endocrinol Metab. 2009, 94, 876-883). For the subtype of ovarial endometriosis, an overexpression of AKR1C3 mRNA has been described (T. Smuc et al., Mol Cell Endocrinol. 2009 Mar. 25; 301(1-2): 59-64).

There is a great need to identify novel inhibitors of the enzyme aldo-keto reductase 1C3 (AKR1C3) (synonyms: type 5 17β-hydroxysteroid dehydrogenase or prostaglandin F synthase), since inhibitors have potential for the treatment of hormone-dependent disorders such as, for example, endometriosis, but also for the treatment of hormone-independent disorders (M. C. Byrns, Y. Jin, T. M. Penning, Journal of Steroid Biochemistry and Molecular Biology (2010); A. L. Lovering et. al., Cancer Res 64(5), 1802-1810). In addition to endometriosis, this also includes prostate cancer (K. M. Fung et al., Endocr Relat Cancer 13(1), 169-180), prostate hyperplasia (R. O. Roberts et al., Prostate 66(4), 392-404), endometrial carcinoma (T. L. Rizner et al., Mol Cell Endocrinol 2006 248(1-2), 126-135), polycystic ovary syndrome (K. Qin et al., J Endocrinol Metab 2006, 91(1), 270-276), lung carcinoma (Q. Lan et al., Carcinogenesis 2004, 25(11), 2177-2181), non-Hodgkin lymphoma (Q. Lan et al., Hum Genet 2007, 121(2), 161-168), hair loss (L. Colombe et al., Exp Dermatol 2007, 16(9), 762-769), adiposity (P. A. Svensson et al., Cell Mol Biol Lett 2008, 13(4), 599-613), bladder carcinoma (J. D. Figueroa, Carcinogenesis 2008, 29(10), 1955-1962), chronic myeloid leukaemia (J. Birthwistle, Mutat Res 2009, 662(1-2), 67-74), renal cell carcinoma (J. T. Azzarello, Int J Clin Exp Pathol 2009, 3(2), 147-155), breast cancer (M. C. Byrns, J Steroid Biochem Mol Biol 2010, 118(3), 177-187), premature sexual maturity (C. He, Hum Genet 2010, 128(5), 515-527) and chronic obstructive pulmonary disease (S. Pierrou, Am J Respir Crit Care 2007, 175(6), 577-586).

Some inhibitors of AKR1C3 are known (review: Joanna M Day, Helena J Tutill, Atul Purohit and Michael J Reed, Endocrine-Related Cancer (2008) 15, 665-692). A steroidal substance that has been described is, for example, EM-1404, which is based on the oestratriene skeleton having a spirolactone unit in position 17 (F. Labrie et al. U.S. Pat. No. 6,541,463, 2003).

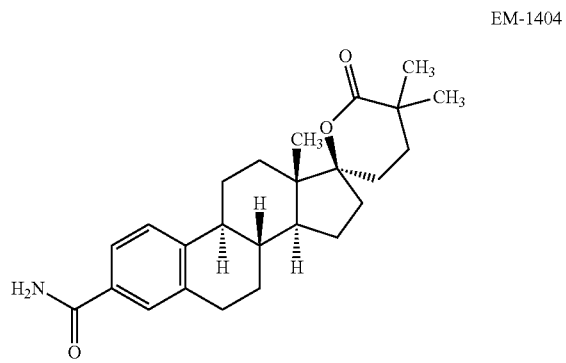

EM-1404

Further steroidal substances having a lactone unit are found in P. Bydal, Van Luu-The, F. Labrie, D. Poirier, European Journal of Medicinal Chemistry 2009, 44, 632-644. Fluorinated oestratriene derivatives have been described in D. Deluca, G. Moller, A. Rosinus, W. Elger, A. Hillisch, J. Adamski, Mol. Cell. Endocrinol. 2006, 248, 218-224.

The compounds according to the invention are substances based on an oestra-1,3,5(10),16-tetraene skeleton substituted by an aromatic heterocycle in position 17 and an aminocarbonyl group in position 3. S. E. Barrie et al. U.S. Pat. No. 5,604,213 describe 17-(3-pyridyl)estra-1,3,5(10), 16-tetraen-3-ol derivates as 17α-hydroxylase/C17-20 lyase (Cyp17A1) inhibitors. In particular, the substance 17-(3-pyridyl)estra-1,3,5(10),16-tetraen-3-ol is reported. However, U.S. Pat. No. 5,604,213 does not describe any 17-(3-pyridyl)estra-1,3,5(10),16-tetraene derivatives substituted by an aminocarbonyl group in the 3-position. The compounds according to the invention claimed here additionally have a carboxyl group as functional group, resulting in a further structural difference to the substances described in U.S. Pat. No. 5,604,213. Surprisingly, it has now been found that the compounds according to the invention claimed herein are potent inhibitors of AKR1C3 (cf. Example 31) and at the same time inhibit Cyp17A1 only very weakly, if at all (cf. Example 32).

Estra-1,3,5(10),16-tetraene derivatives substituted by an aminocarbonyl (—CONH$_2$) group in position 3 are described in US 2005/0203075. However, these derivatives are not substituted by a heterocycle in position 17 of the estra-1,3,5(10),16-tetraene skeleton.

A review of 17-pyridyl- and 17-pyrimidylandrostane derivatives described as Cyp17A1 inhibitors is found in V. M. Moreira et al. Current Medicinal Chemistry, 2008 Vol. 15, No. 9.

It is an object of the present invention to provide alternative substances acting as AKR1C3 inhibitors. Compared to the known AKR1C3 inhibitor EM-1404, the novel AKR1C3 inhibitors claimed herein additionally show a markedly improved solubility in water (cf. Example 33). As a consequence, it is much easier to formulate the compounds according to the invention in aqueous administration media.

The present invention provides compounds of the formula (I):

(I)

[Structure of formula (I): steroid-like scaffold with substituents R1, R2 on pyridine ring, R5, R6, CH3, H, R3, R4 on fused ring system, and R7-N(R8)-C(=O)- group on aromatic ring]

in which
R1 and R2
  independently of one another represent hydrogen, fluorine, chlorine, nitrile, trifluoromethyl, pentafluoroethyl, methoxy, ethoxy, trifluoromethoxy, —OCH$_2$CF$_3$, CH$_3$SO$_2$—, CH$_3$CH$_2$SO$_2$—, —(C=O)CH$_3$, carboxyl, C$_1$-C$_4$-alkyl, hydroxy, —CH$_2$OH, —C(CH$_3$)$_2$OH, —CONH$_2$, —(C=O)NH-alkyl, —(C=O)N(CH$_3$)$_2$, —SO$_2$NH$_2$, —SO$_2$NHCH$_3$, —SO$_2$N(CH$_3$)$_2$ or the replacement of a C—H group in the pyridine ring by a nitrogen atom and
R3 and R4
  represent hydrogen or
  R3 represents hydroxy, fluorine, methoxy or ethoxy and R4 represents hydrogen or
  R3 represents hydrogen and R4 represents hydroxy, fluorine, methoxy or ethoxy and
R5 and R6
  represent hydrogen or
  R5 represents fluorine, hydroxy, methoxy or ethoxy and R6 represents hydrogen or
  R5 represents hydrogen and R6 represents fluorine and
R7
  represents hydrogen, C$_1$-C$_4$-alkyl, C$_3$-C$_6$-cycloalkyl, cyclopropylmethyl, trifluoromethyl or 2,2,2-trifluoroethyl and
R8
  represents —CR$^a$R$^b$—COOH where
    R$^a$ and R$^b$ independently of one another represent hydrogen, methyl, ethyl or
    R$^a$ and R$^b$ together represent —(CH$_2$)$_n$— where n=2, 3, 4 or 5, where up to 4 hydrogen atoms of the CH$_2$ groups may be replaced by fluorine atoms or
    R$^a$ and R$^b$ together represent —CH$_2$—O—CH$_2$—, —CH$_2$—NH—CH$_2$—, —CH$_2$—N(CH$_3$)—CH$_2$—, —CH$_2$CH$_2$—O—CH$_2$CH$_2$—, —CH$_2$CH$_2$—NH—CH$_2$CH$_2$—, —CH$_2$CH$_2$—N(CH$_3$)—CH$_2$CH$_2$— or
    R$^a$ represents hydrogen, methyl or ethyl and R$^b$ together with R7 represents —(CH$_2$)$_n$— where n=1, 2, 3, 4, where individual or up to 4 hydrogen atoms of the CH$_2$ groups may be replaced by fluorine atoms or
    R$^a$ together with R7 represents —CH$_2$—O—CH$_2$CH$_2$—, —CH$_2$—N(CH$_3$)—CH$_2$CH$_2$— and R$^b$ represents hydrogen, methyl or ethyl or represents —CR$^c$R$^d$—CR$^e$R$^f$—COOH where
  R$^c$, R$^d$, R$^e$, R$^f$ represent hydrogen or
  R$^c$, R$^d$ independently of one another represent methyl, ethyl or together represent —(CH$_2$)$_n$— where n=2, 3, 4, 5 or —CH$_2$CH$_2$—O—CH$_2$CH$_2$— and R$^e$, R$^f$ represent hydrogen or
  R$^c$, R$^d$ represent hydrogen and R$^e$, R$^f$ independently of one another represent methyl, ethyl or together represent —(CH$_2$)$_n$— where n=2, 3, 4, 5, —CH$_2$CH$_2$—O—CH$_2$CH$_2$—, —CH$_2$CH$_2$—NH—CH$_2$CH$_2$—, —CH$_2$CH$_2$—N(CH$_3$)—CH$_2$CH$_2$— or —CH$_2$—O—CH$_2$— or
  R$^c$ represents methyl, ethyl, trifluoromethyl and R$^d$, R$^e$ and R$^f$ represent hydrogen or
  R$^c$, R$^d$ and R$^f$ represent hydrogen and R$^e$ represents methyl, ethyl, trifluoromethyl, hydroxy or methoxy or
  R$^c$ and R$^e$ together represent —(CH$_2$)$_n$— where n=1, 2, 3 or 4 and R$^d$ and R$^f$ represent hydrogen or represents —CH$_2$—CH$_2$—CHR$^g$—COOH where
  R$^g$ represents hydrogen or
  R$^g$ and R7 together represent —CH$_2$— or —CH$_2$CH$_2$— and their salts, solvates and solvates of the salts.

The invention likewise provides compounds of the formula (II) and the formula (III)

(II)

[Structure of formula (II): similar steroid scaffold with R1 on pyridine, R5, CH3, R7, R8, R3, R4 substituents]

(III)

[Structure of formula (III): similar steroid scaffold with pyrimidine ring, R5, CH3, R7, R8, R3, R4 substituents]

in which
R1
  represents hydrogen, fluorine, chlorine, nitrile, methoxy, ethoxy, trifluoromethoxy, methyl, ethyl, trifluoromethyl, —(C=O)CH$_3$ and
R3 and R4
  represent hydrogen or
  R3 represents hydroxy and R4 represents hydrogen or
  R3 represents hydrogen and R4 represents hydroxy and
R5
  represents hydrogen or fluorine and R7
  represents hydrogen or $C_1$-$C_4$-alkyl and
R8
  represents —$CR^aR^b$—COOH where
    $R^a$ and $R^b$ independently of one another represent hydrogen, methyl or ethyl or
    $R^a$ and $R^b$ together represent —$(CH_2)_n$— where n=2, 3, 4 or 5 or
    $R^a$ represents hydrogen and $R^b$ together with R7 represents —$(CH_2)_n$— where n=3 or 4 or
  represents —$CR^cR^d$—$CR^eR^f$—COOH where
    $R^c$, $R^d$, $R^e$, $R^f$ represent hydrogen or
    $R^c$, $R^d$ represent hydrogen and $R^e$, $R^f$ independently of one another represent methyl, ethyl or together represent —$(CH_2)$n- where n=2, 3, 4, 5 or —$CH_2CH_2$—O—$CH_2CH_2$— or
    $R^c$ represents methyl or ethyl and $R^d$, $R^e$ and $R^f$ represent hydrogen or
    $R^c$ and $R^e$ together represent —$(CH_2)_n$— where n=1, 2, 3 or 4 and $R^d$ and $R^f$ represent hydrogen or
  represents —$CH_2$—$CH_2$—$CHR^g$—COOH where
    $R^g$ represents hydrogen or
    $R^g$ and R7 together represent —$CH_2CH_2$—
and their salts, solvates and solvates of the salts.

The invention also provides compounds of the formula (II) and the formula (III) in which
R1
  represents hydrogen, fluorine, chlorine, nitrile, methoxy, trifluoromethyl and
R3 and R4
  represent hydrogen or
  R3 represents hydroxy and R4 represents hydrogen or
  R3 represents hydrogen and R4 represents hydroxy and
R5
  represents hydrogen or fluorine and
R7
  represents hydrogen, methyl or ethyl and
R8
  represents —$CR^aR^b$—COOH where
    $R^a$ and $R^b$ independently of one another represent hydrogen, methyl or ethyl or
    $R^a$ represents hydrogen and $R^b$ together with R7 represents —$(CH_2)_n$— where n=3 or 4 or
  represents —$CR^cR^d$—$CR^eR^f$—COOH where
    $R^c$, $R^d$, $R^e$, $R^f$ represent hydrogen or
    $R^c$, $R^d$ represent hydrogen and $R^e$, $R^f$ independently of one another represent methyl or ethyl or together represent —$(CH_2)$n- where n=2, 4, 5 or represent —$CH_2CH_2$—O—$CH_2CH_2$— or
    $R^c$ represents methyl and $R^d$, $R^e$ and $R^f$ represent hydrogen or
    $R^c$ and $R^e$ together represent —$(CH_2)_n$— where n=3 or 4 and $R^d$ and $R^f$ represent hydrogen or
  represents —$CH_2$—$CH_2$—$CHR^g$—COOH where
    $R^g$ represents hydrogen or
    $R^g$ and R7 together represent —$CH_2CH_2$—
and their salts, solvates and solvates of the salts.

Moreover, the invention provides compounds of the formula (II) and the formula (III) in which
R1
  represents hydrogen, fluorine, methoxy, trifluoromethyl and
R3 and R4
  represent hydrogen or
  R3 represents hydroxy and R4 represents hydrogen or
  R3 represents hydrogen and R4 represents hydroxy and
R5
  represents hydrogen or fluorine and
R7
  represents hydrogen or methyl and
R8
  represents —$CR^aR^b$—COOH where
    $R^a$ and $R^b$ independently of one another represent hydrogen or methyl or
    $R^a$ represents hydrogen and $R^b$ together with R7 represents —$(CH_2)_3$— or
  represents —$CR^cR^d$—$CR^eR^f$—COOH where
    $R^c$, $R^d$, $R^e$, $R^f$ represent hydrogen, or
    $R^c$ and $R^d$ represent hydrogen and $R^e$ and $R^f$ represent methyl or together represent —$(CH_2)$n- where n=2 or 4 or represent —$CH_2CH_2$—O—$CH_2CH_2$— or
    $R^c$ represents methyl and $R^d$, $R^e$ and $R^f$ represent hydrogen or
    $R^c$ and $R^e$ together represent —$(CH_2)_3$— and $R^d$ and $R^f$ represent hydrogen or
  represents —$CH_2$—$CH_2$—$CHR^g$—COOH where
    $R^g$ represents hydrogen or
    $R^g$ and R7 represent —$CH_2CH_2$—
and their salts, solvates and solvates of the salts.

Furthermore, the invention provides the compounds
4-[({[17-(5-fluoropyridin-3-yl)estra-1,3,5(10),16-tetraen-3-yl]carbonyl}amino)-methyl]-3,4,5,6-tetrahydro-2H-pyran-4-carboxylic acid
N-{[17-(5-fluoropyridin-3-yl)estra-1,3,5(10),16-tetraen-3-yl]carbonyl}-N-methyl-β-alanine
1-[({[17-(5-fluoropyridin-3-yl)estra-1,3,5(10),16-tetraen-3-yl]carbonyl}amino)-methyl]cyclopropan-1-carboxylic acid
1-[({[17-(5-fluoropyridin-3-yl)estra-1,3,5(10),16-tetraen-3-yl]carbonyl}amino)-methyl]cyclopentane-1-carboxylic acid
3-({[17-(5-fluoropyridin-3-yl)estra-1,3,5(10),16-tetraen-3-yl]carbonyl}amino)-2,2-dimethylpropanoic acid
1-{[17-(5-fluoropyridin-3-yl)estra-1,3,5(10),16-tetraen-3-yl]carbonyl}piperidine-4-carboxylic acid
N-{[17-(5-fluoropyridin-3-yl)estra-1,3,5(10),16-tetraen-3-yl]carbonyl}-2-methylalanine
4-({[17-(5-fluoropyridin-3-yl)estra-1,3,5(10),16-tetraen-3-yl]carbonyl}amino)butanoic acid
N-{[17-(5-fluoropyridin-3-yl)estra-1,3,5(10),16-tetraen-3-yl]carbonyl}-β-alanine
N-{[17-(5-fluoropyridin-3-yl)estra-1,3,5(10),16-tetraen-3-yl]carbonyl}glycine
(1R*,2S*)-2-({[17-(5-fluoropyridin-3-yl)estra-1,3,5(10),16-tetraen-3-yl]carbonyl}-amino)cyclopentane-1-carboxylic acid
(S)-3-({[17-(5-fluoropyridin-3-yl)estra-1,3,5(10),16-tetraen-3-yl]carbonyl}amino)-butanoic acid
(R)-3-({[17-(5-fluoropyridin-3-yl)estra-1,3,5(10),16-tetraen-3-yl]carbonyl}amino)-butanoic acid
3-({[17-(5-methoxypyridin-3-yl)estra-1,3,5(10),16-tetraen-3-yl]carbonyl}amino)-2,2-dimethylpropanoic acid
N-{[17-(5-methoxypyridin-3-yl)estra-1,3,5(10),16-tetraen-3-yl]carbonyl}-β-alanine
N-{[17-(5-methoxypyridin-3-yl)estra-1,3,5(10),16-tetraen-3-yl]carbonyl}-N-methyl-β-alanine
N-{[17-(pyrimidin-5-yl)estra-1,3,5(10),16-tetraen-3-yl]carbonyl}-β-alanine
4-({[17-(pyrimidin-5-yl)estra-1,3,5(10),16-tetraen-3-yl]carbonyl}amino)butanoic acid
N-methyl-N-{[17-(pyrimidin-5-yl)estra-1,3,5(10),16-tetraen-3-yl]carbonyl}-β-alanine 2,2-dimethyl-3-({[17-(pyrimidin-5-yl)estra-1,3,5(10),16-tetraen-3-yl]carbonyl}-amino)propanoic acid N-({17-[5-(trifluoromethyl)pyridin-3-yl]estra-1,3,5(10),16-tetraen-3-yl}carbonyl)-β-alanine N-methyl-N-({17-[5-(trifluoromethyl)pyridin-3-yl]estra-1,3,5(10),16-tetraen-3-yl}-carbonyl)-β-alanine N-{[17-(5-fluoropyridin-3-yl)estra-1,3,5(10),16-tetraen-3-yl]carbonyl}-L-proline N-{[17-(5-fluoropyridin-3-yl)estra-1,3,5(10),16-tetraen-3-yl]carbonyl}-D-proline 4-({[11β-fluoro-17-(5-fluoropyridin-3-yl)estra-1,3,5(10),16-tetraen-3-yl]carbonyl}-amino)butanoic acid N-{[17-(5-fluoropyridin-3-yl)-15α-hydroxyestra-1,3,5(10),16-tetraen-3-yl]carbonyl}-N-methyl-β-alanine N-{[17-(5-fluoropyridin-3-yl)-15β-hydroxyestra-1,3,5(10),16-tetraen-3-yl]carbonyl}-N-methyl-β-alanine N-methyl-N-{[17-(6-methylpyridazin-4-yl)estra-1,3,5(10),16-tetraen-3-yl]carbonyl}-β-alanine N-methyl-N-{[17-(3-pyridin-3-yl)estra-1,3,5(10),16-tetraen-3-yl]carbonyl}-β-alanine 4-({[17-(5-methoxypyridin-3-yl)estra-1,3,5(10),16-tetraen-3-yl]carbonyl}amino)-butanoic acid and their salts, solvates and solvates of the salts.

It has been found that the estra-1,3,5(10),16-tetraene-3-carbonylamino derivatives provided by the invention act as AKR1C3 inhibitors. For the major part of the structural range claimed, these substances show strong inhibition of AKR1C3 in vitro (IC$_{50}$ values of less than 50 nM) and predominantly even IC$_{50}$ values <20 nM. In addition, these derivatives display only a very low inhibition of Cyp17A1, if any.

Compounds according to the invention are the compounds of the formula (I) and their salts, solvates and solvates of the salts, the compounds of the formulae mentioned below comprised by formula (I) and their salts, solvates and solvates of the salts and the compounds mentioned below as working examples and comprised by formula (I) and their salts, solvates and solvates of the salts, provided the compounds mentioned below and comprised by formula (I) are not already salts, solvates and solvates of the salts.

Depending on their structure, the compounds according to the invention can exist in stereoisomeric forms (diastereomers). In compounds of the formula (I), stereocentres can be present in radical R8 (and, if R7 and R8 together form a cycle, also in this cycle). Accordingly the invention comprises the diastereomers and their respective mixtures. From such mixtures of diastereomers, the stereoisomerically uniform components can be isolated in a known manner.

If the compounds according to the invention can be present in tautomeric forms, the present invention comprises all tautomeric forms.

Preferred salts in the context of the present invention are physiologically acceptable salts of the compounds according to the invention. However, the invention also comprises salts which for their part are not suitable for pharmaceutical applications, but which can be used, for example, for the isolation or purification of the compounds according to the invention.

Physiologically acceptable salts of the compounds according to the invention include acid addition salts of mineral acids, carboxylic acids and sulphonic acids, for example salts of hydrochloric acid, hydrobromic acid, sulphuric acid, phosphoric acid, methanesulphonic acid, ethanesulphonic acid, toluenesulphonic acid, benzenesulphonic acid, acetic acid, formic acid, trifluoroacetic acid, propionic acid, lactic acid, tartaric acid, malic acid, citric acid, fumaric acid, maleic acid and benzoic acid.

Physiologically acceptable salts of the compounds according to the invention also include salts of customary bases, such as, by way of example and by way of preference, alkali metal salts (for example sodium salts and potassium salts), alkaline earth metal salts (for example calcium salts and magnesium salts) and ammonium salts derived from ammonia or organic amines having 1 to 16 carbon atoms such as, by way of example and by way of preference, ethylamine, diethylamine, triethylamine, ethyldiisopropylamine, monoethanolamine, diethanolamine, triethanolamine, dicyclohexylamine, dimethylaminoethanol, procain, dibenzylamine, N-methylmorpholine, arginine, lysine, ethylenediamine and N-methylpiperidine.

In the context of the invention, solvates are those forms of the compounds according to the invention which, in the solid or liquid state, form a complex by coordination with solvent molecules. Hydrates are a specific form of the solvates where the coordination is with water. In the context of the present invention, preferred solvates are hydrates.

Moreover, the present invention also comprises prodrugs of the compounds according to the invention. The term "prodrugs" includes compounds which for their part may be biologically active or inactive but which, during the time they spend in the body, are converted into compounds according to the invention (for example metabolically or hydrolytically).

In the context of the present invention, unless specified differently, the substituents have the following meanings:

$C_1$-$C_4$-Alkyl represents a straight-chain or branched alkyl radical having 1 to 4 carbon atoms, by way of example and by way of preference methyl, ethyl, propyl, butyl, isopropyl, tert-butyl, isobutyl.

$C_3$-$C_6$-Cycloalkyl represents a cycloalkyl group having 3 to 6 carbon atoms, where the ring may also be partially unsaturated, by way of example and by way of preference cyclopropyl, cyclobutyl, cyclopentyl and cyclohexyl.

The invention furthermore provides processes for preparing the compounds of the formula (I) according to the invention. The preparation of the compounds (I) according to the invention can be illustrated by the synthesis schemes below:

Some of the compounds according to the invention can be prepared starting with methyl 17-oxoestra-1,3,5(10)-triene-3-carboxylate, which is known from the literature (Steroids, 1995, 60, 3, 299-306) (synthesis scheme 1):

The conversion into Intermediate 1 is carried out by using trifluoromethanesulphonic anhydride or N,N-bis(trifluoromethanesulphonyl)aniline in the presence of a base such as pyridine, 2,6-dimethylpyridine or 2,6-di-tert-butylpyridine or in the presence of a tertiary amine such as triethylamine or diisopropylethylamine, or by using alkali metal hexamethylsilazanes or lithium diisopropylamide (LDA) (J. Med. Chem., 1995, 38, 2463-2471, J. Org. Chem., 1985, 50, 1990-1992, JACS, 2009, 131, 9014-9019, Archiv der Pharmazie (Weinheim, Germany), 2001, 334, 12, 373-374). Preference is given to the reaction with trifluoromethanesulphonic anhydride in the presence of 2,6-di-tert-butylpyridine in dichloromethane.

The Intermediates 2 are prepared using the Suzuki reaction, which is known to the person skilled in the art. To this end, Intermediate 1 is reacted with a nitrogen-containing aromatic boronic acid, a boronic ester such as, for example, a boronic acid pinacole ester, an MIDA boronate (D. M. Knapp et al. J. Am. Chem. Soc. 2009, 131, 6961) or with a trifluoroborate salt (G. A. Molander et al., J. Org. Chem.

2009, 74, 973). Suitable catalysts are a large number of palladium-containing catalysts such as, for example, tetrakis (triphenylphosphine)palladium(0), bis(triphenylphosphine) palladium(II) dichloride or [1,3-bis(2,6-diisopropylphenyl) imidazol-2-ylidene](3-chloropyridyl)palladium(II) dichloride (CAS 905459-27-0). Alternatively, it is possible to use a palladium-containing source such as, for example, palladium(II) acetate, palladium(II) chloride or Pd(dba)$_2$ in combination with a phosphorous-containing ligand such as, for example, triphenylphosphine, SPhos (D. M. Knapp et. al., J. Am. Chem. Soc. 2009, 131, 6961) or RuPhos (G. A. Molander, J. Org. Chem. 2009, 74, 973). The boronic acids are preferably reacted in the presence of tetrakis(triphenylphosphine)palladium(0) or [1,3-bis(2,6-diisopropylphenyl) imidazol-2-ylidene](3-chloropyridyl)palladium(II) dichloride.

The Intermediates 3 are prepared by hydrolysis of the methyl ester according to methods known to the person skilled in the art. To this end, Intermediate 2 is, in a solvent such as tetrahydrofuran (THF), methanol or dimethyl sulphoxide (DMSO) or in a mixture of methanol and THF, admixed with aqueous sodium hydroxide solution or an aqueous lithium hydroxide solution. If required, the mixture is heated. The reaction in THF and methanol in the presence of aqueous sodium hydroxide solution or aqueous lithium hydroxide solution at 40° C. is preferred.

The preparation of the exemplary compounds is carried out in two steps starting with Intermediates 3 by an amide coupling with an ester of an amino acid and by subsequent conversion of the carboxylic ester into the carboxylic acid. Suitable for the amide coupling (Step A) are reagents known to the person skilled in the art such as, for example, N,N'-dicyclohexylcarbodiimide (DCC), N-[3-(dimethylamino)propyl]-N-ethylcarbodiimide hydrochloride (EDC) [CAS 25952-53-8] or HATU (O-(7-azabenzotriazol-1-yl)-N,N,N',N'-tetramethyluronium hexafluorophosphonate. Additionally, it is also possible to employ, as additives, reagents such as 1H-benzotriazol-1-ol hydrate (HOBt hydrate [CAS 123333-53-9]) or 4-dimethylaminopyridine (DMAP). Suitable for use as bases are, for example, pyridine, triethylamine or diisopropylethylamine. Preference is given to the reaction using EDC, HOBt hydrate and triethylamine. For the conversion of the carboxylic ester into the carboxylic acid (Step B), it is possible to use—if the ester is, for example, a methyl, ethyl or benzylester—hydrolysis methods as described for the preparation of Intermediate 3. If the ester is a tert-butyl carboxylate, this can be converted into the carboxylic acid by methods known to the person skilled in the art, such as, for example, by reaction with trifluoroacetic acid in dichloromethane or chloroform or by reaction with hydrogen chloride in 1,4-dioxane. The reaction with trifluoroacetic acid in dichloromethane is preferred.

Snythesis scheme 1

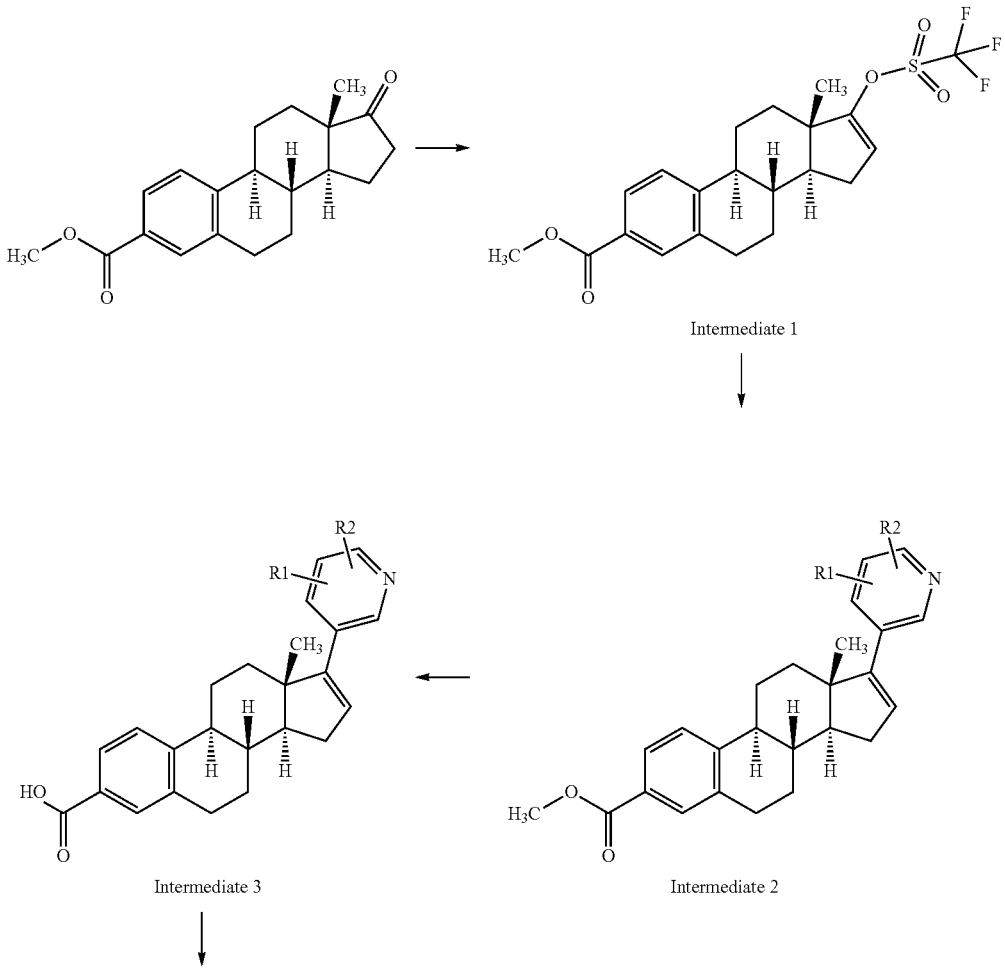

Intermediate 1

Intermediate 3

Intermediate 2

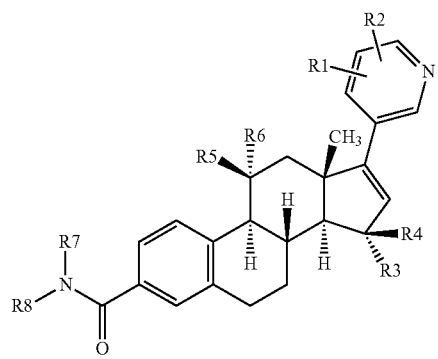

Subset of the exemplary compounds
where R3, R4, R5, R6 = H

A subset of the compounds of the formula (I) according to the invention where R5=F and R6=H can be prepared as described in synthesis scheme 2:

Using acetic anhydride and pyridine in the presence of 4-dimethylaminopyridine (DMAP) in dichloromethane, 3,11α-dihydroxyestra-1,3,5(10)-trien-17-one is converted into Intermediate 4. The conversion into Intermediate 5 is carried out using sodium bicarbonate in methanol. The reaction of Intermediate 5 with 1,1,2,2,3,3,4,4,4-nonafluorobutane-1-sulphonyl fluoride and potassium carbonate yields Intermediate 6, which is converted with palladium(II) acetate, 1,3-bis(diphenylphosphino)propane, triethylamine in methanol and DMSO in an autoclave under a carbon monoxide atmosphere into Intermediate 7. The conversion into Intermediate 8 is carried out using methods as described for the preparation of Intermediate 1. The transformation of Intermediate 8 into Intermediate 9 is carried out using methods as described for the preparation of Intermediate 2. Using potassium carbonate and methanol, Intermediate 9 is hydrolysed to give Intermediate 10. The transformation into Intermediate 11 is carried out using 1,8-diazabicyclo[5.4.0]undec-7-ene and 1,1,2,2,3,3,4,4,4-nonafluorobutane-1-sulphonyl fluoride in THF. The hydrolysis of Intermediate 11 to give Intermediate 12 is carried out using conditions as described for the preparation of Intermediate 3. Preference is given to the reaction in THF and methanol in the presence of aqueous lithium hydroxide solution. The preparation of a subset of the exemplary compounds starting with Intermediate 12 is carried out analogously to the preparation of the exemplary compounds starting with Intermediate 3 as described in synthesis scheme 1.

Synthesis scheme 2

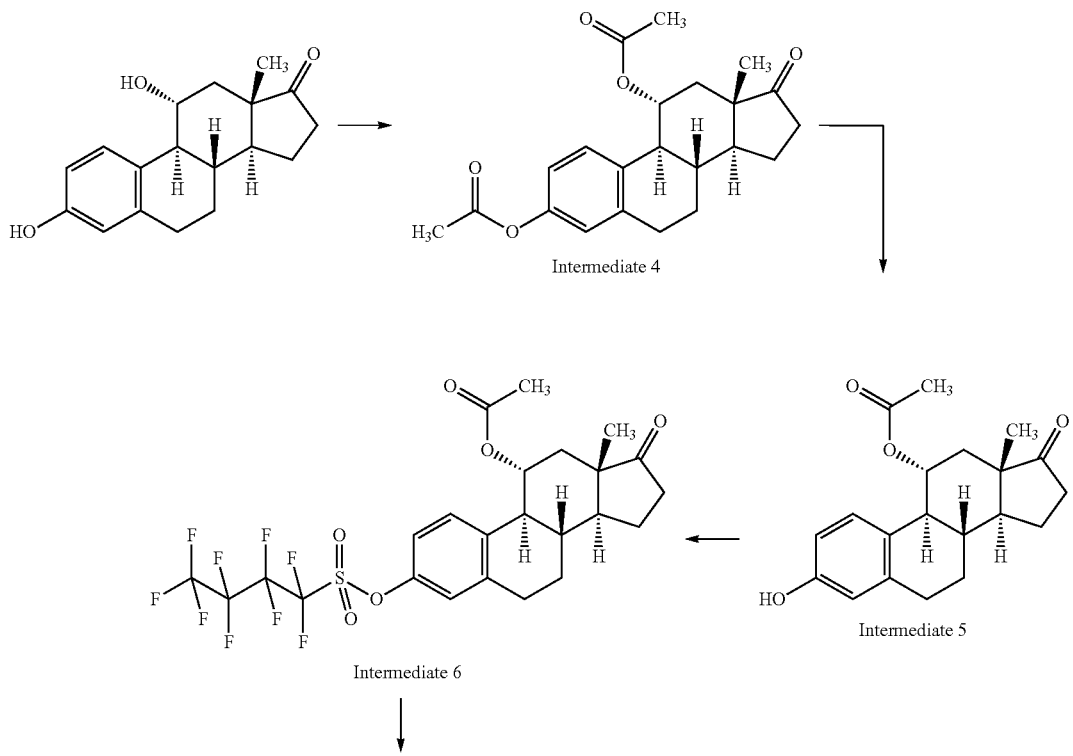

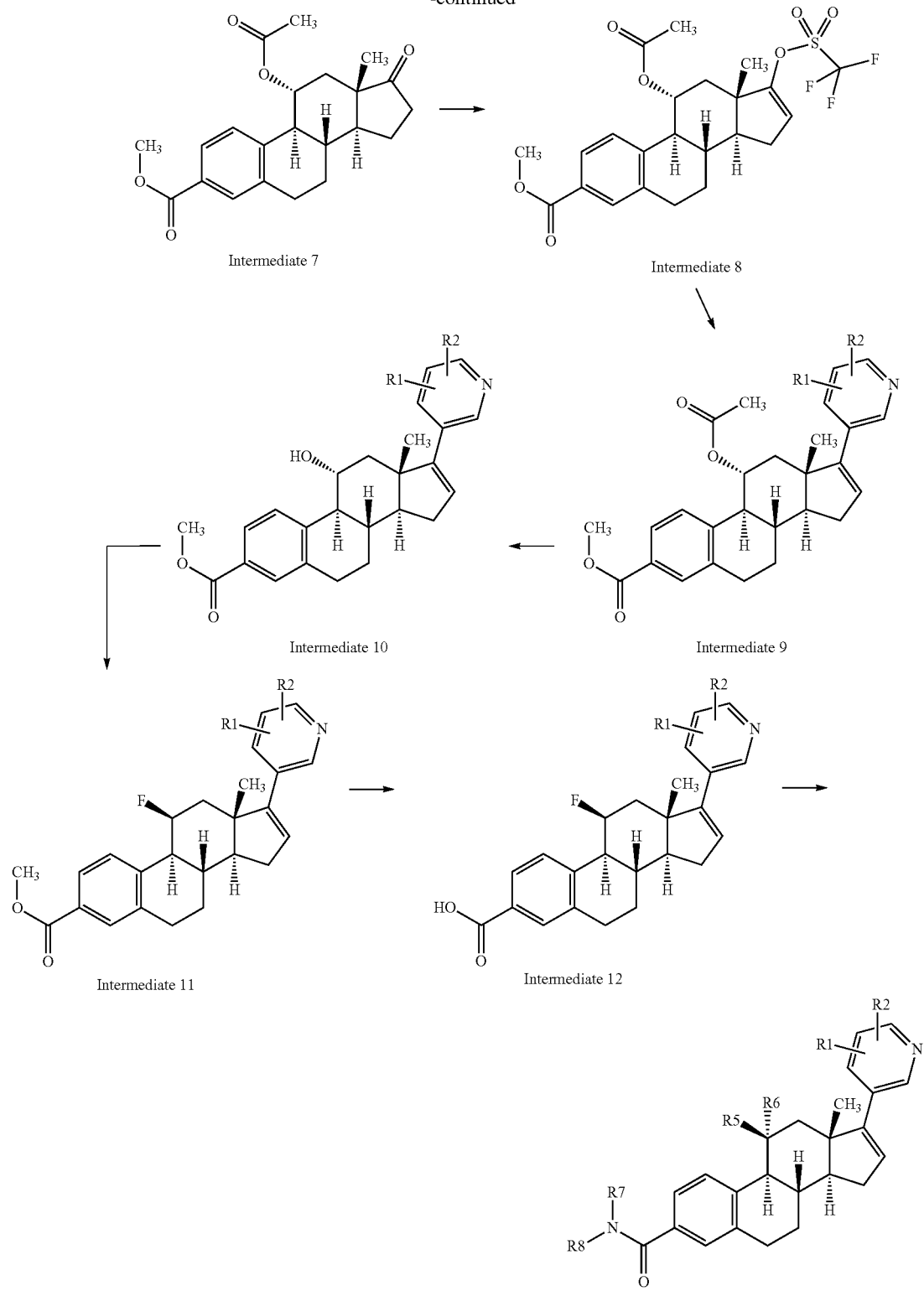

Subset of the exemplary compounds
where R5 = F, R6 = H

A subset of the compounds of the formula (I) according to the invention having the substituent definition R3=OH and R4=H or R3=H and R4=OH can be prepared as illustrated in synthesis scheme 3. The reaction is carried out using microorganisms, for example certain suitable fungus strains allowing a regio- and stereoselective hydroxylation. In this manner, it is possible, for example, to introduce hydroxyl groups into the 15-position of the steroid skeleton in a regio- and stereoselective manner. The resulting 15-OH derivatives are exemplary compounds for the purpose of the invention and can further also be modified further in subsequent chemical reactions.

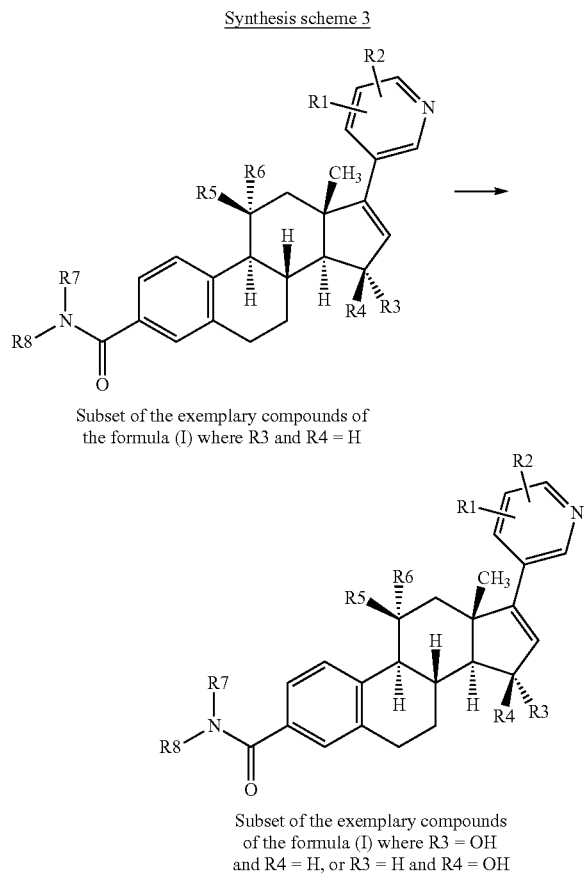

Synthesis scheme 3

Subset of the exemplary compounds of the formula (I) where R3 and R4 = H

Subset of the exemplary compounds of the formula (I) where R3 = OH and R4 = H, or R3 = H and R4 = OH In an unforeseeable manner, the compounds according to the invention display a useful spectrum of pharmacological activity and advantageous pharmacokinetic properties. They are therefore suitable for use as medicaments for the treatment and/or prophylaxis of diseases in humans and animals. For the purpose of the present invention, the term "treatment" includes prophylaxis. The pharmaceutical efficacy of the compounds according to the invention can be explained by its action as AKR1C3 inhibitor. Accordingly, the compounds according to the invention are particularly suitable for the treatment and/or prophylaxis of endometriosis, of uterine leiomyomas, of uterine bleeding disorders, of dysmenorrhoea, of prostate carcinoma, of prostate hyperplasia, of acne, of seborrhoea, of hair loss, of premature sexual maturity, of polycystic ovary syndrome, of breast cancer, of lung cancer, of endometrial carcinoma, of renal cell carcinoma, of bladder carcinoma, of non-Hodgkin lymphomas, of chronic obstructive pulmonary disease (COPD), of adiposity or of inflammatory pain.

The present invention furthermore provides the use of the compounds according to the invention for preparing a medicament for the treatment and/or prophylaxis of disorders, in particular the disorders mentioned above.

The present invention furthermore provides a method for the treatment and/or prophylaxis of disorders, in particular the disorders mentioned above, using an effective amount of the compounds according to the invention.

The present invention furthermore provides the use of the compounds according to the invention for the treatment and/or prophylaxis of disorders, in particular the disorders mentioned above.

The present invention furthermore provides the compounds according to the invention for use in a method for the treatment and/or prophylaxis of the disorders mentioned above.

The present invention furthermore provides medicaments comprising at least one compound according to the invention and at least one or more further active compounds, in particular for the treatment and/or prophylaxis of the disorders mentioned above. The following suitable active compounds for combinations may be mentioned by way of example and by way of preference: selective oestrogen receptor modulators (SERMs), oestrogen receptor (ER) antagonists, aromatase inhibitors, 17β HSD1 inhibitors, steroid sulphatase (STS) inhibitors, GnRH agonists and antagonists, kisspeptin receptor (KISSR) antagonists, selective androgen receptor modulators (SARMs), androgens, 5α-reductase inhibitors, selective progesterone receptor modulators (SPRMs), gestagens, antigestagens, oral contraceptives, inhibitors of mitogen activating protein (MAP) kinases and inhibitors of the MAP kinases kinases (Mkk3/6, Mek1/2, Erk1/2), inhibitors of the protein kinases B (PKBα/β/γ; Akt1/2/3), inhibitors of the phosphoinositide 3-kinases (PI3K), inhibitors of the cyclin-dependent kinase (CDK1/2), inhibitors of the hypoxia-induced signal path (HIF1alpha inhibitors, activators of prolyl hydroxylases), histone deacetylase (HDAC) inhibitors, prostaglandin F receptor (FP) (PTGFR) antagonists and non-steroidal antiflammatory drugs (NSAIDs).

The invention also relates to pharmaceutical preparations comprising at least one compound of the general formula I (or physiologically acceptable addition salts thereof with organic or inorganic acids) and the use of these compounds for preparing medicaments, in particular for the indications mentioned above.

The compounds can be used for the indications mentioned above, both after oral and after parenteral administration.

The compounds according to the invention can have systemic and/or local action. For this purpose, they can be administered in a suitable way, for example orally, parenterally, pulmonarly, nasally, sublingually, lingually, buccally, rectally, dermally, transdermally, conjunctivally, otically or as an implant or stent.

For these routes of application, the compounds according to the invention can be administered in suitable dosage forms.

Dosage forms that function according to the prior art, with rapid and/or modified release of the compounds according to the invention, containing the compounds according to the invention in crystalline and/or amorphisized and/or dissolved form, are suitable for oral administration, for example tablets (uncoated or coated tablets, for example with enteric coatings or coatings with delayed dissolution or insoluble coatings, which control the release of the compound according to the invention), tablets that disintegrate rapidly in the oral cavity or films/wafers, films/lyophylisates, capsules (for example hard-gelatin or soft-gelatin capsules), sugar-coated tablets, granules, pellets, powders, emulsions, suspensions, aerosols or solutions.

Parenteral administration can take place with avoidance of an absorption step (for example intravenously, intra-arterially, intracardially, intraspinally or intralumbally) or with inclusion of absorption (for example intramuscularly, subcutaneously, intracutaneously, percutaneously or intraperitoneally). Suitable dosage forms for parenteral administration are inter alia injection and infusion preparations in the form of solutions, suspensions, emulsions, lyophilisates or sterile powders.

Suitable dosage forms for the other routes of administration are, for example, pharmaceutical forms for inhalation (inter alia powder inhalers, nebulizers), nasal drops, solutions, and sprays; tablets for lingual, sublingual or buccal administration, films/wafers or capsules, suppositories, ear or eye preparations, vaginal capsules, aqueous suspensions (lotions, shaking mixtures), lipophilic suspensions, ointments, creams, transdermal therapeutic systems (such as, for example, patches), milk, pastes, foams, dusting powders, implants, intrauterine systems, vaginal rings or stents.

The compounds according to the invention can be converted into the stated dosage forms. This can take place in a manner that is known per se, by mixing with inert, non-toxic, pharmaceutically suitable auxiliaries. These auxiliaries include inter alia vehicles (for example microcrystalline cellulose, lactose, mannitol), solvents (for example liquid polyethylene glycols), emulsifiers and dispersants or wetting agents (for example sodium dodecylsulphate, polyoxysorbitan oleate), binders (for example polyvinylpyrrolidone), synthetic and natural polymers (for example albumin), stabilizers (for example antioxidants such as, for example, ascorbic acid), colorants (for example inorganic pigments such as, for example, iron oxides) and taste and/or odour correctants.

The present invention further relates to medicinal products comprising at least one compound according to the invention, usually together with one or more inert, non-toxic, pharmaceutically suitable auxiliaries, and their use for the purposes stated above.

In the case of oral administration, the amount per day is from about 0.01 to 100 mg/kg of body weight. The amount of a compound of the general formula I to be administered varies over a wide range and can cover every effective amount. Depending on the condition to be treated and the method of administration, the amount of the compound administered can be 0.01-100 mg/kg of body weight per day.

Nevertheless, it may optionally be necessary to deviate from the stated amounts, mainly depending on body weight, route of administration, individual response to the active substance, type of preparation and time point or interval in which administration takes place. Thus, in some cases it may be sufficient to use less than the aforementioned minimum amount, whereas in other cases the stated upper limit must be exceeded. In the case of administration of relatively large amounts, it may be advisable to divide these into several individual doses throughout the day.

The percentages in the following tests and examples are, unless stated otherwise, percentages by weight; parts are parts by weight. Proportions of solvents, dilution ratios and information about concentration for liquid/liquid solutions relate in each case to volume.

List of Abbreviations, Chemistry

Abbreviations and Acronyms:

| DMAP | 4-Dimethylaminopyridine |
| DMF | Dimethylformamide |
| DMSO | Dimethyl sulphoxide |
| h | Hour(s) |
| HPLC | High-pressure, high-performance liquid chromatography |
| LC-MS | Liquid chromatography-coupled mass spectroscopy |
| ES-MS | Electrospray mass spectroscopy |
| min | Minute(s) |
| MS | Mass spectroscopy |
| NMR | Nuclear magnetic resonance spectroscopy |
| RT | Room temperature |
| TFA | Trifluoroacetic acid |
| THF | Tetrahydrofuran |

Purification of the Compounds According to the Invention

In some cases the compounds according to the invention could be purified by preparative HPLC, for example using an autopurifier apparatus from Waters (detection of the compounds by UV detection and electrospray ionization) in combination with commercially available, prepacked HPLC columns (for example XBridge column (from Waters), C18, 5 μm, 30×100 mm). The solvent system used was acetonitrile/water with addition of formic acid. Further additives known to the person skilled in the art, such as, for example, ammonia, ammonium acetate or trifluoroacetic acid, may be used. Instead of acetonitrile, it is also possible to use, for example, methanol.

In some cases, the following method was used for preparative HPLC separation:

| System: | Waters auto purification system: pump 2545, sample manager 2767, CFO, DAD 2996, ELSD 2424, SQD |
| Column: | XBridge C18 5 μm 100 × 30 mm |
| Solvent: | A = $H_2O$ + 0.1% by volume formic acid (99%) |
| | B = Acetonitrile |
| Gradient: | 0-1 min 1% B, 1-8 min 1-99% B, 8-10 min 99% B |
| Flow rate: | 50 ml/min |
| Temperature: | RT |
| Injection: | 1 × 2.5 ml |
| Detection: | DAD scan range 210-400 nm |
| | MS ESI+, ESI−, scan range 160-1000 m/z |

Freeze-drying or vacuum centrifugation was used for removing the HPLC solvent mixture. If the resulting compounds are present as TFA salts or formate salts, they can be converted by standard laboratory procedures known to the person skilled in the art into the respective free bases.

In some cases, the compounds according to the invention could be purified by chromatography on silica gel. For this purpose, for example, prepacked silica gel cartridges (for example ISOLUTE® Flash silica gel cartridges (Separtis) were used in combination with a chromatograph (for example, the FLASHMASTER™ II chromatograph (Argonaut/Biotage)) and chromatography solvents or solvent mixtures such as, for example, hexane, ethyl acetate and dichloromethane and methanol.

Structural Analysis of the Compounds According to the Invention:

In some cases, the compounds according to the invention were analysed by LC-MS:

In some cases, the following analytical method was used:

Instrument: Waters Acquity UPLC-MS SQD; column: Acquity UPLC BEH C18 1.7 50×2.1 mm; mobile phase A: water+0.1% by volume of formic acid (99%), mobile phase B: acetonitrile; gradient: 0-1.6 min 1-99% B, 1.6-2.0 min 99% B; flow rate 0.8 ml/min; temperature: 60° C.; injection: 2 μl; DAD scan: 210-400 nm The following symbols are used in the NMR data of the compounds according to the invention:

| | |
|---|---|
| s | Singlet |
| d | Doublet |
| t | Triplet |
| q | Quartet |
| quin | Quintet |
| m | Multiplet |
| br | Broad |
| mc | Centred multiplet |

Synthesis of the Compounds According to the Invention

Intermediate 1

Methyl 17-{[(trifluoromethyl)sulphonyl]oxy}estra-1,3,5(10),16-tetraene-3-carboxylate

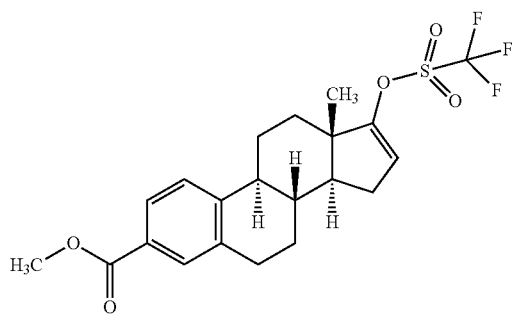

3.2 ml of trifluoromethanesulphonic anhydride were added dropwise to a mixture of 5.00 g (16.0 mmol) of methyl 17-oxoestra-1,3,5(10)-triene-3-carboxylate (Steroids, 1995, 60, 3, 299-306) in 100 ml of dichloromethane and 5.3 ml of 2,6-di-tert-butylpyridine, and the mixture was stirred at RT for 20 h. The mixture was carefully poured into 250 ml of saturated aqueous sodium bicarbonate solution and stirred for 40 min, the phases were separated, the aqueous phase was extracted twice with dichloromethane and the combined organic phases were washed with saturated sodium bicarbonate solution and sodium chloride solution, dried over sodium sulphate and concentrated. Trituration with hexane gave 4.55 g of the title compound as a solid.

$^1$H-NMR (300 MHz, CHLOROFORM-d): δ [ppm]=1.01 (s, 3H), 1.37-1.74 (m, 5H), 1.81 (td, 1H), 1.88-2.02 (m, 2H), 2.05-2.19 (m, 1H), 2.27-2.55 (m, 3H), 2.83-3.11 (m, 2H), 3.90 (s, 3H), 5.63 (dd, 1H), 7.32 (d, 1H), 7.68-7.90 (m, 2H).

Intermediate 2-a

Methyl 17-(5-fluoropyridin-3-yl)estra-1,3,5(10),16-tetraene-3-carboxylate

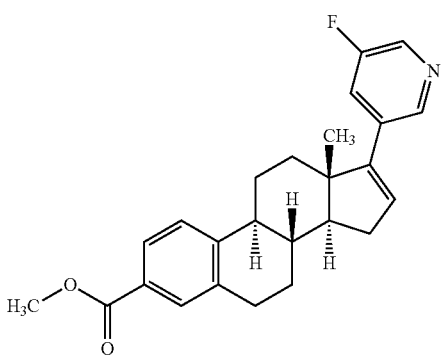

8.00 g (2.25 mmol) of methyl 17-{[(trifluoromethyl)sulphonyl]oxy}estra-1,3,5(10),16-tetraene-3-carboxylate and 3.55 g (1.4 equiv.) of 5-fluoropyridine-3-boronic acid were initially charged in 60 ml of toluene and 40 ml of ethanol. 1.53 g (2.0 equiv.) of lithium chloride, 24 ml of 2M aqueous sodium carbonate solution and 1.04 g (5 mol %) of tetrakis(triphenylphosphine)palladium(0) were then added, and the mixture was heated at 100° C. for 3.5 h. Water was added, the mixture was extracted three times with ethyl acetate and the extracts were washed with saturated sodium bicarbonate solution and sodium chloride solution and concentrated. Purification by column chromatography on silica gel (hexane/ethyl acetate) gave 5.5 g (78% of theory) of the title compound.

$^1$H-NMR (400 MHz, CHLOROFORM-d): δ [ppm]=1.06 (s, 3H), 1.47-1.63 (m, 1H), 1.63-1.78 (m, 3H), 1.84 (td, 1H), 1.98-2.06 (m, 1H), 2.13-2.26 (m, 2H), 2.35-2.51 (m, 3H), 2.98 (dd, 2H), 3.90 (s, 3H), 6.10 (dd, 1H), 7.32-7.44 (m, 2H), 7.76-7.86 (m, 2H), 8.36 (br. s., 1H), 8.48 (s, 1H).

Intermediate 2-b

Methyl 17-(5-methoxypyridin-3-yl)estra-1,3,5(10),16-tetraene-3-carboxylate

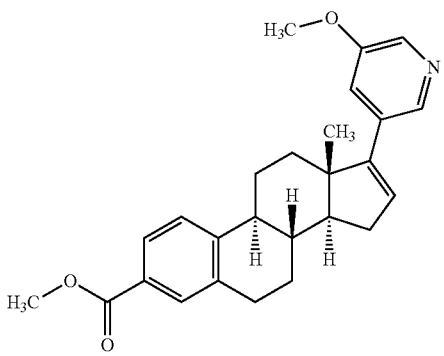

Analogously to the preparation of intermediate 2-a, 2.00 g (4.50 mmol) of Intermediate 1 were reacted with 0.96 g (1.4 equiv.) of (5-methoxypyridin-3-yl)boronic acid in the presence of 260 mg of tetrakis(triphenylphosphine)palladium(0) at 100° C. overnight to give 1.4 g (76% of theory) of the title compound.

¹H-NMR (300 MHz, CHLOROFORM-d): δ [ppm]=1.05 (s, 3H), 1.43-1.60 (m, 1H), 1.62-1.89 (m, 4H), 1.95-2.08 (m, 1H), 2.10-2.25 (m, 2H), 2.30-2.53 (m, 3H), 2.98 (dd, 2H), 3.88 (s, 3H), 3.90 (s, 3H), 6.00-6.08 (m, 1H), 7.16-7.22 (m, 1H), 7.35 (d, 1H), 7.75-7.83 (m, 2H), 8.20 (d, 1H), 8.28 (d, 1H).

Intermediate 2-c

Methyl 17-(pyrimidin-5-yl)estra-1,3,5(10),16-tetraene-3-carboxylate

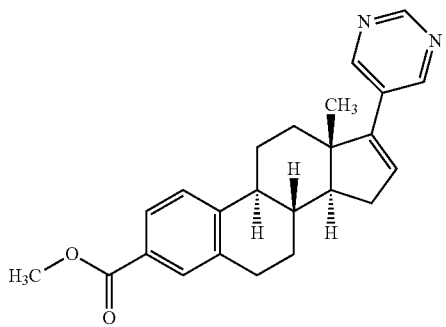

Analogously to the preparation of Intermediate 2-a, 3.00 g (6.75 mmol) of Intermediate 1 were reacted with 1.17 g (1.4 equiv.) pyrimidin-5-ylboronic acid in the presence of 390 mg of tetrakis(triphenylphosphine)palladium(0) at 100° C. overnight to give 1.70 g (64% of theory) of the title compound.

¹H-NMR (400 MHz, CHLOROFORM-d): δ [ppm]=1.06 (s, 3H), 1.47-1.59 (m, 1H), 1.65-1.80 (m, 3H), 1.85 (td, 1H), 1.98-2.06 (m, 1H), 2.12-2.25 (m, 2H), 2.36-2.53 (m, 3H), 2.98 (dd, 2H), 3.90 (s, 3H), 6.14 (dd, 1H), 7.35 (d, 1H), 7.76-7.85 (m, 2H), 8.76 (s, 2H), 9.09 (s, 1H).

Intermediate 2-d

Methyl 17-[5-(trifluoromethyl)pyridin-3-yl]estra-1,3,5(10),16-tetraene-3-carboxylate

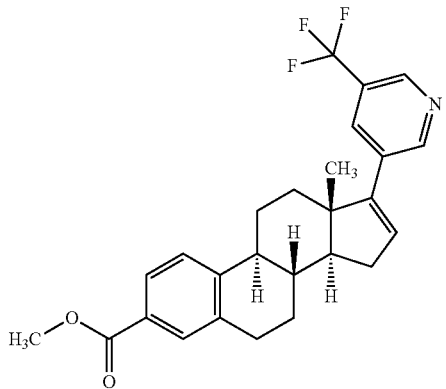

Analogously to the preparation of Intermediate 2-a, 1.66 g (3.74 mmol) of Intermediate 1 were reacted with 1.00 g (1.4 equiv.) of [5-(trifluoromethyl)pyridin-3-yl]boronic acid in the presence of 216 mg of tetrakis(triphenylphosphine)palladium(0) at 100° C. overnight to give 1.20 g (73% of theory) of the title compound.

¹H-NMR (300 MHz, CHLOROFORM-d): δ [ppm]=1.08 (s, 3H), 1.49-1.89 (m, 6H), 1.97-2.09 (m, 1H), 2.09-2.28 (m, 2H), 2.35-2.54 (m, 3H), 2.98 (dd, 2H), 3.90 (s, 3H), 6.15 (dd, 1H), 7.36 (s, 1H), 7.77-7.85 (m, 2H), 7.88 (s, 1H), 8.83 (s, 2H).

Intermediate 2-e

Methyl 17-(6-methylpyridazin-4-yl)estra-1,3,5(10),16-tetraene-3-carboxylate

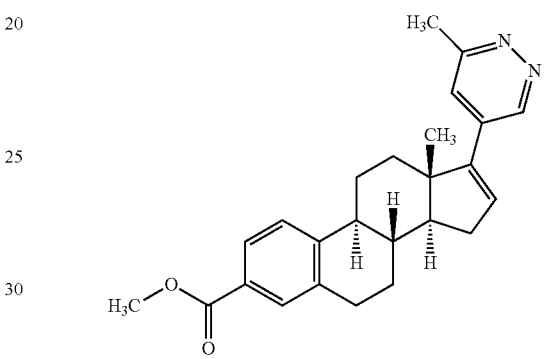

Analogously to the preparation of Intermediate 2-a, 180 mg (3.74 mmol) of Intermediate 1 were reacted with 125 mg (1.4 equiv.) of 3-methyl-5-(4,4,5,5-tetramethyl-1,3,2-dioxaborolan-2-yl)pyridazine in the presence of 14 mg of bis(triphenylphosphine)palladium(II) chloride at 100° C. Aqueous work-up as described in the preparation of Intermediate 2-a gave 201 mg of a crude product which was used without further purification for preparing Intermediate 3-e.

Intermediate 2-f

Methyl 17-(pyridin-3-yl)estra-1,3,5(10),16-tetraene-3-carboxylate

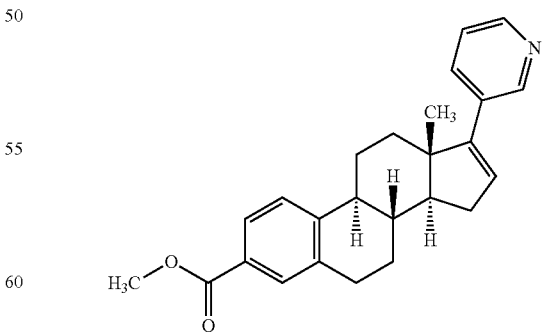

Analogously to the preparation of Intermediate 2-a, 500 mg (1.13 mmol) of Intermediate 1 were reacted with 194 mg (1.4 equiv.) of pyridin-3-ylboronic acid in the presence of 39 mg of bis(triphenylphosphine)palladium(II) chloride at 100°

C. for 18 h. Aqueous work-up gave 462 mg of a crude product which was used without further purification for preparing Intermediate 3-f.

Intermediate 3-a 17-(5-Fluoropyridin-3-yl)estra-1,3,5(10),16-tetraene-3-carboxylic acid

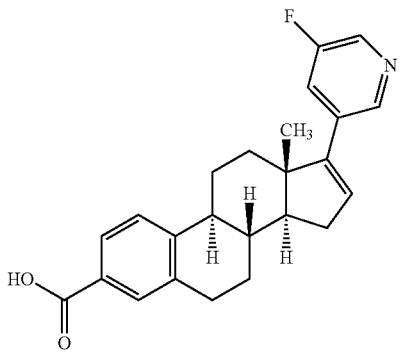

372 mg (0.95 mmol) of Intermediate 2-a were initially charged in 50 ml of THF and 3 ml of methanol. A solution of 120 mg of lithium hydroxide in 3 ml of water was added, and the mixture was stirred at RT for 18 h. Another 5 equiv. of lithium hydroxide were added and the mixture was stirred at RT for 24 h and at 40° C. for 18 h. The mixture was diluted with water, acidified to pH 4 using 10% strength aqueous citric acid solution, ethyl acetate was added and the solid was filtered off, giving, after washing of the solid with ethyl acetate and water and drying, 153 mg (43% of theory) of the title compound. The organic phase of the filtrate was separated off and the aqueous phase was extracted twice with ethyl acetate. Washing of the combined organic phases with sodium chloride solution, drying over sodium sulphate and concentration gave a residue which was triturated with diethyl ether. Drying gave a further 143 mg (40% of theory) of the title compound.

$^1$H-NMR (300 MHz, DMSO-$d_6$): δ [ppm]=0.99 (s, 3H), 1.38-1.78 (m, 5H), 1.83-1.97 (m, 1H), 2.05-2.21 (m, 2H), 2.25-2.43 (m, 3H), 2.89 (dd, 2H), 6.27 (dd, 1H), 7.36 (d, 1H), 7.58-7.72 (m, 3H), 8.43 (d, 1H), 8.49 (t, 1H).

Intermediate 3-b 17-(5-Methoxypyridin-3-yl)estra-1,3,5(10),16-tetraene-3-carboxylic acid

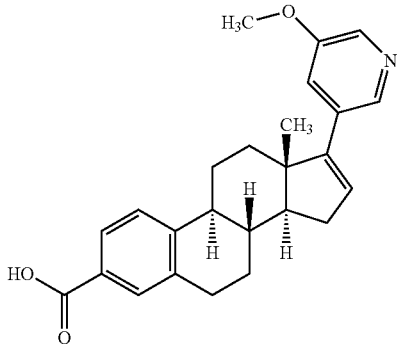

A solution of 1.4 g (3.47 mmol) of methyl 17-(5-methoxypyridin-3-yl)estra-1,3,5(10),16-tetraene-3-carboxylate in 30 ml of THF, 4 ml of methanol and 8.7 ml of 2M aqueous sodium hydroxide solution were stirred at RT overnight and then warmed at 40° C. for 8.5 h. The mixture was diluted with water, acidified to pH=4 with 10% strength citric acid solution and extracted three times with ethyl acetate, and the organic phases were washed with sodium chloride solution and concentrated. Trituration of the crude product with ether gave 1.2 g (89% of theory) of the title compound.

$^1$H-NMR (300 MHz, DMSO-$d_6$): δ [ppm]=0.98 (s, 3H), 1.34-1.81 (m, 5H), 1.84-1.97 (m, 1H), 2.03-2.19 (m, 2H), 2.21-2.43 (m, 3H), 2.89 (dd, 2H), 3.81 (s, 3H), 6.12-6.20 (m, 1H), 7.20-7.29 (m, 1H), 7.36 (d, 1H), 7.59-7.70 (m, 2H), 8.15 (d, 1H), 8.20 (d, 1H).

Intermediate 3-c 17-(Pyrimidin-5-yl)estra-1,3,5(10),16-tetraene-3-carboxylic acid

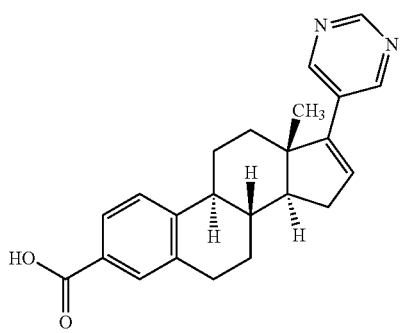

A mixture of 1.70 g (4.54 mmol) of methyl 17-(pyrimidin-5-yl)estra-1,3,5(10),16-tetraene-3-carboxylate, 40 ml of THF, 11.3 ml of 2M aqueous sodium hydroxide solution and 5 ml of methanol was stirred at RT overnight, then 40° C. for 8.5 h and then at RT overnight. The mixture was diluted with water and acidified to pH=4 with 10% strength citric acid solution, and ethyl acetate was added. The insoluble solid was filtered off and dried. This gave 1.3 g (79% of theory) of the title compound.

$^1$H-NMR (300 MHz, DMSO-$d_6$): δ [ppm]=0.99 (s, 3H), 1.39-1.79 (m, 5H), 1.84-1.97 (m, 1H), 2.06-2.21 (m, 2H), 2.26-2.44 (m, 3H), 2.89 (dd, 2H), 6.28-6.33 (m, 1H), 7.36 (d, 1H), 7.59-7.69 (m, 2H), 8.83 (s, 2H), 9.04 (s, 1H), 12.7 (br. s., 1H).

Intermediate 3-d

17-[5-(Trifluoromethyl)pyridin-3-yl]estra-1,3,5(10),16-tetraene-3-carboxylic acid

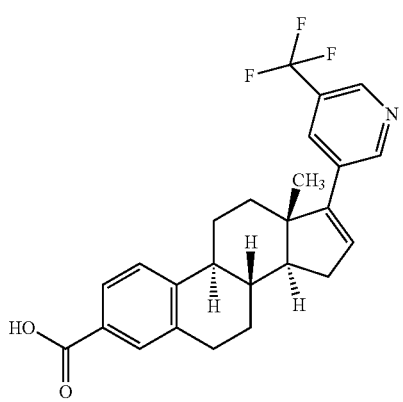

1.2 g of methyl 17-[5-(trifluoromethyl)pyridin-3-yl]estra-1,3,5(10),16-tetraene-3-carboxylate were initially charged in 12 ml of THF, a solution of 0.23 g of lithium hydroxide in 12 ml of water was added and the mixture was stirred at 40° C. overnight. The mixture was diluted with water, acidified to pH=4 with 10% strength citric acid solution and extracted three times with ethyl acetate. The extracts were washed with sodium chloride solution and concentrated, and the residue was triturated with diethyl ether. This gave 850 mg of the title compound as a solid.

$^1$H-NMR (400 MHz, DMSO-d$_6$): δ [ppm]=1.01 (s, 3H), 1.37-1.50 (m, 1H), 1.50-1.69 (m, 3H), 1.76 (td, 1H), 1.86-1.95 (m, 1H), 2.08-2.19 (m, 2H), 2.27-2.44 (m, 3H), 2.90 (dd, 2H), 6.36 (dd, 1H), 7.36 (d, 1H), 7.61-7.68 (m, 2H), 8.04 (s, 1H), 8.82-8.86 (m, 1H), 8.90 (d, 1H), 12.7 (br. s., 1H).

Intermediate 3-e 17-(6-Methylpyridazin-4-yl)estra-1,3,5(10),16-tetraene-3-carboxylic acid

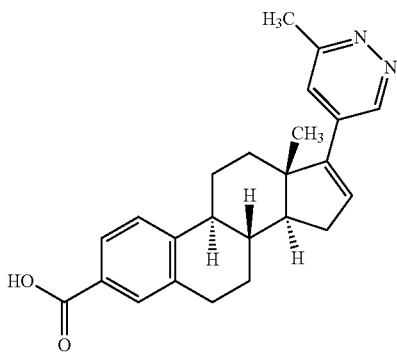

201 mg of methyl 17-(6-methylpyridazin-4-yl)estra-1,3,5(10),16-tetraene-3-carboxylate (crude product) were initially charged in 3 ml of THF and 0.5 ml of methanol, 1.3 ml of a 2M aqueous sodium hydroxide solution were added and the mixture was stirred at 40° C. overnight. The mixture was diluted with water, acidified to pH=4 with 10% strength citric acid solution and extracted three times with ethyl acetate, and the extracts were concentrated. Purification of the residue by preparative HPLC gave 42 mg of the title compound as a crude product.

C$_{24}$H$_{26}$N$_2$O$_2$ (374.5). MS-ES+ mass found: 374.20.

Intermediate 3-f 17-(Pyridin-3-yl)estra-1,3,5(10),16-tetraene-3-carboxylic acid

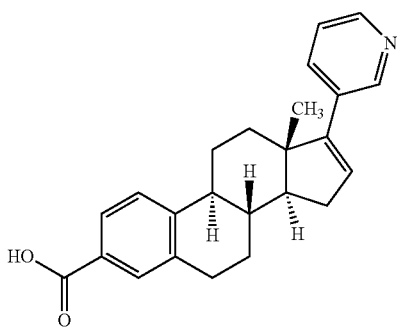

462 mg of methyl 17-(pyridin-3-yl)estra-1,3,5(10),16-tetraene-3-carboxylate (crude product) were dissolved in 4 ml of THF and 1 ml of methanol, 3 ml of a 2M aqueous sodium hydroxide solution were added and the mixture was stirred at 40° C. overnight. The mixture was diluted with water and acidified to pH=4 with 10% strength citric acid solution, and ethyl acetate was added. The insoluble solid that remained was filtered off, washed with water and ethyl acetate and dried under reduced pressure. This gave 375 mg (84% of theory) of the title compound.

C$_{24}$H$_{25}$NO$_2$ (359.47). MS-ES+ mass found: 359.00.

$^1$H-NMR (300 MHz, DMSO-d$_6$): δ [ppm]=0.99 (s, 3H), 1.35-1.78 (m, 6H), 1.84-1.96 (m, 1H), 2.03-2.18 (m, 2H), 2.21-2.44 (m, 4H), 2.89 (dd, 2H), 6.10-6.14 (m, 1H), 7.29-7.39 (m, 2H), 7.57-7.68 (m, 2H), 7.77 (dt, 1H), 8.42 (dd, 1H), 8.59 (d, 1H).

Intermediate 4

17-Oxoestra-1,3,5(10)-triene-3,11α-diyl diacetate

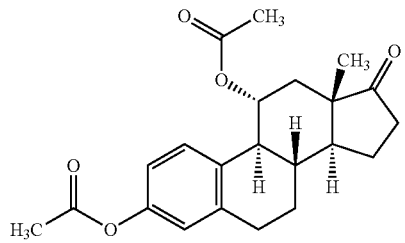

At RT, 13.2 ml (4.0 equiv.) of acetic anhydride were added dropwise to a solution of 10.0 g (34.9 mmol) of 3,11α-dihydroxyestra-1,3,5(10)-trien-17-one in 100 ml of dichloromethane, and the reaction mixture was cooled to 5° C. 14.1 ml of pyridine were then added dropwise, and after 10 min the mixture was allowed to warm to RT and stirred for 4 h. A spatula tip of DMAP was added, and the mixture was stirred at RT for 72 h. The mixture was poured into 500 ml of water, the phases were separated, the aqueous phase was extracted with dichloromethane and the combined organic phases were washed with 1M hydrochloric acid, water and sodium chloride solution, dried over sodium sulphate and concentrated. This gave 12.9 g (99% of theory) of a white solid.

$^1$H-NMR (400 MHz, DMSO-d$_6$): δ [ppm]=0.81 (s, 3H), 1.29 (t, 1H), 1.43-1.72 (m, 4H), 1.79-2.00 (m, 2H), 2.00-2.06 (m, 3H), 2.06-2.19 (m, 2H), 2.19-2.25 (m, 3H), 2.42-2.57 (m, superimposed by DMSO signal), 2.76 (t, 2H), 5.26 (td, 1H), 6.82-6.89 (m, 2H), 6.97 (d, 1H).

Intermediate 5

3-Hydroxy-17-oxoestra-1,3,5(10)-trien-11α-yl acetate

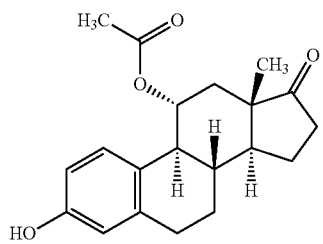

14.6 g (5 equiv.) of sodium bicarbonate were added to 12.9 g (34.7 mmol) of 17-oxoestra-1,3,5(10)-triene-3,11α-diyl diacetate in 100 ml of methanol, and the mixture was stirred at RT overnight. 100 ml of water and 1 ml of 1M hydrochloric acid were added, and the mixture was stirred for 30 min. The mixture was extracted four times with ethyl acetate. A solid precipitated from the organic phase, which solid was filtered off with suction and dried. This gave 3.74 g (33% of theory) of the title compound. In addition, 6.39 g (56% of theory) of the title compound were isolated by washing the organic phase with saturated sodium chloride solution, drying over sodium sulphate, concentration, trituration of the residue with ethyl acetate, filtration with suction and drying under reduced pressure.

$^1$H-NMR (300 MHz, DMSO-$d_6$): δ [ppm]=0.79 (s, 3H), 1.25 (t, 1H), 1.36-1.69 (m, 4H), 1.75-1.98 (m, 2H), 1.98-2.18 (m, 5H), 2.34-2.43 (m), 2.68 (t, 2H), 5.16 (td, 1H), 6.43-6.55 (m, 2H), 6.76 (d, 1H), 9.07 (s, 1H).

Intermediate 6

3-{[(1,1,2,2,3,3,4,4,4-Nonafluorobutyl)sulphonyl]oxy}-17-oxoestra-1,3,5(10)-trien-11α-yl acetate

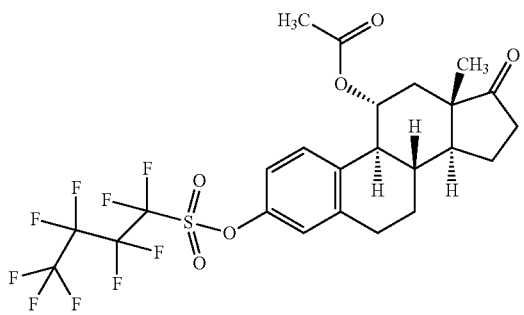

12.8 g (3 equiv.) of potassium carbonate and 6.5 ml (1.2 equiv.) of 1,1,2,2,3,3,4,4,4-nonafluorobutane-1-sulphonyl fluoride were added to a solution of 10.1 g (31 mmol) of 3-hydroxy-17-oxoestra-1,3,5(10)-trien-11α-yl acetate in 20 ml of THF, and the mixture was heated under reflux for 4 h and stirred at RT for 18 h. Another 1 ml of 1,1,2,2,3,3,4,4,4-nonafluorobutane-1-sulphonyl fluoride was added, and the mixture was heated under reflux for 3 h. Water and saturated sodium chloride solution were added, the mixture was stirred for 20 min, the phases were separated and the aqueous phase was extracted three times with in each case 50 ml of ethyl acetate. The combined organic phases were washed twice with in each case 50 ml of water and twice with 50 ml of saturated sodium chloride solution, dried over sodium sulphate, filtered and concentrated. Purification by column chromatography on silica gel (hexane/ethyl acetate) gave 18.1 g (96% of theory) of 3-{[(1,1,2,2,3,3,4,4,4-nonafluorobutyl)sulphonyl]oxy}-17-oxoestra-1,3,5(10)-trien-11α-yl acetate.

$^1$H-NMR (400 MHz, DMSO-$d_6$): δ [ppm]=0.85 (s, 3H), 1.26-1.37 (m, 1H), 1.47-1.76 (m, 4H), 1.83-2.02 (m, 2H), 2.03-2.25 (m, 5H, contains s at 2.06 ppm), 2.41-2.47 (m), 2.59 (t, 1H), 2.77-2.95 (m, 2H), 5.29 (td, 1H), 7.15 (d, 1H), 7.23-7.29 (m, 2H).

Intermediate 7

Methyl 11α-acetoxy-17-oxoestra-1,3,5(10)-triene-3-carboxylate

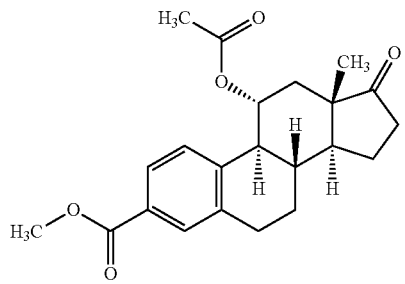

Under argon, 10.0 g (16.4 mmol) of 3-{[(1,1,2,2,3,3,4,4,4-nonafluorobutyl)sulphonyl]oxy}-17-oxoestra-1,3,5(10)-trien-11α-yl acetate, 230 mg (6 mol %) of palladium(II) acetate and 440 mg (6 mol %) of 1,3-bis(diphenylphosphino)propane were initially charged in an autoclave, and 36 ml of methanol, 54 ml of DMSO and 6 ml of triethylamine were added. The reaction mixture was flushed three times with carbon monoxide and stirred at RT at a carbon monoxide pressure of 7.5 bar for 30 min. The autoclave was then vented and evacuated, and the mixture was stirred at 70° C. at a carbon monoxide pressure of 6.8 bar for 3.5 h. The mixture was concentrated and the residue was taken up in water and ethyl acetate. The phases were separated and the aqueous phase was extracted twice with ethyl acetate. The combined organic phases were washed with 1M hydrochloric acid and saturated sodium bicarbonate solution, dried over sodium sulphate and concentrated. Purification of the residue by column chromatography on silica gel (hexane/ethyl acetate) gave 5.96 g (98% of theory) of the title compound as a solid.

$^1$H-NMR (300 MHz, DMSO-$d_6$): δ [ppm]=0.81 (s, 3H), 1.29 (t, 1H), 1.40-1.76 (m, 4H), 1.78-2.00 (m, 2H), 2.00-2.21 (m, 5H, contains s at 2.03 ppm), 2.37-2.52 (m, obscured by DMSO signal), 2.59 (t, 1H), 2.72-2.93 (m, 2H), 3.79 (s, 3H), 5.29 (td, 1H), 5.23-5.38 (m, 1H), 7.08 (d, 1H), 7.68-7.75 (m, 2H).

Intermediate 8

Methyl 11α-acetoxy-17-{[(trifluoromethyl)sulphonyl]oxy}estra-1,3,5(10),16-tetraene-3-carboxylate

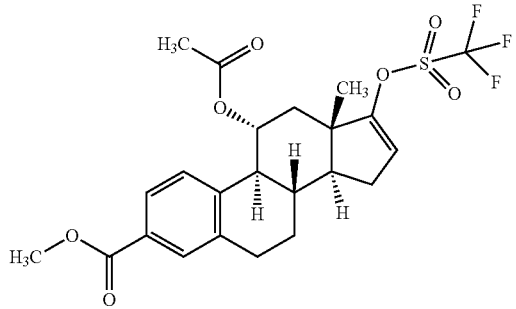

Analogously to preparation of Intermediate 1, 2.96 g (7.99 mmol) of methyl 11α-acetoxy-17-oxoestra-1,3,5(10)-triene-3-carboxylate were converted in 5.13 g of the title compound as a crude product (contained residual 2,6-di-tert-butylpyridine).

$^1$H-NMR (300 MHz, DMSO-d$_6$): δ [ppm]=0.93 (s, 3H), 1.41-1.71 (m, 3H), 1.71-1.87 (m, 1H), 1.87-2.16 (m, 5H, contains s at 2.03 ppm), 2.16-2.40 (m, 2H), 2.67 (t, 1H), 2.74-2.93 (m, 2H), 3.79 (s, 3H), 5.34 (td, 1H), 5.75-5.82 (m, 1H), 7.03 (d, 1H), 7.67-7.75 (m, 2H).

Intermediate 9

Methyl 11α-acetoxy-17-(5-fluoropyridin-3-yl)estra-1,3,5(10),16-tetraene-3-carboxylate

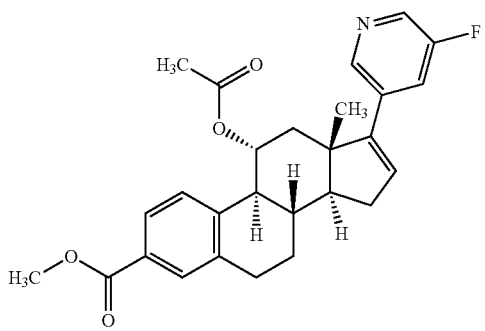

Analogously to Intermediate 2-a, 2.50 g (4.98 mmol) of methyl 11α-acetoxy-17-{[(trifluoromethyl)sulphonyl]oxy}estra-1,3,5(10),16-tetraene-3-carboxylate were reacted with 981 mg (1.4 equiv.) of 5-fluoropyridine-3-boronic acid in the presence of 170 mg (5 mol %) of [1,3-bis(2,6-diisopropylphenyl)imidazol-2-ylidene](3-chloropyridyl)palladium(II) dichloride (PEPPSI™-IPr, CAS 905459-27-0) at reflux temperature over a period of 5 h. This gave 2.62 g of the title compound as a crude product.

Intermediate 10

Methyl 17-(5-fluoropyridin-3-yl)-11α-hydroxyestra-1,3,5(10),16-tetraene-3-carboxylate

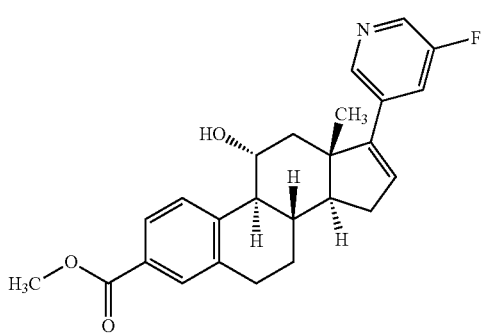

4.0 g (5 equiv.) of potassium carbonate were added to 2.62 g (5.83 mmol) of methyl-11α-acetoxy-17-(5-fluoropyridin-3-yl)estra-1,3,5(10),16-tetraene-3-carboxylate in 40 ml of methanol, and the mixture was stirred at RT for 3 h. The mixture was diluted with water and 1M hydrochloric acid and extracted three times with ethyl acetate. The combined organic phases were washed with water and saturated sodium chloride solution, dried over sodium sulphate and concentrated. Column chromatography on silica gel (hexane/ethyl acetate) gave 1.19 g (50% of theory) of the title compound.

$^1$H-NMR (300 MHz, DMSO-d$_6$, selected signals): δ [ppm]=0.95 (s, 3H), 1.40-1.61 (m, 3H), 2.78-2.97 (m, 2H), 3.79 (s, 3H), 4.06-4.21 (m, 1H), 4.79-4.92 (m, 1H), 6.26 (br. s., 1H), 7.59-7.74 (m, 3H), 8.07 (d, 1H), 8.39-8.54 (m, 2H).

Intermediate 11

Methyl 11β-fluoro-17-(5-fluoropyridin-3-yl)estra-1,3,5(10),16-tetraene-3-carboxylate

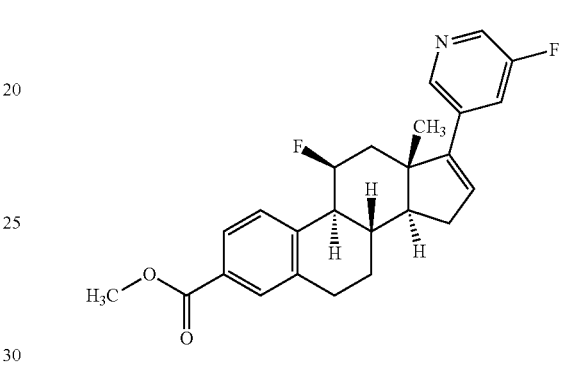

0.52 ml (1.65 equiv.) of 1,8-diazabicyclo[5.4.0]undec-7-ene and 0.58 ml (1.5 equiv.) of 1,1,2,2,3,3,4,4,4-nonafluorobutane-1-sulphonyl fluoride were added dropwise to an ice-cold solution of 531 mg (3.49 mmol) of methyl 17-(5-fluoropyridin-3-yl)-11α-hydroxyestra-1,3,5(10),16-tetraene-3-carboxylate in 15 ml of THF, and the mixture was stirred with ice-bath cooling for 3 h. The mixture was concentrated and the product was purified by column chromatography on silica gel (hexane/ethyl acetate). This gave 747 mg (84% of theory) of the title compound as a crude product.

$^1$H-NMR (300 MHz, DMSO-d$_6$, selected signals): δ [ppm]=2.86-2.97 (m, 2H), 5.57-5.83 (m, 1H), 6.26-6.32 (m, 1H), 7.45-7.53 (m, 1H), 7.65-7.78 (m, 3H), 8.39-8.53 (m, 2H).

Intermediate 12

11β-Fluoro-17-(5-fluoropyridin-3-yl)estra-1,3,5(10),16-tetraene-3-carboxylic acid

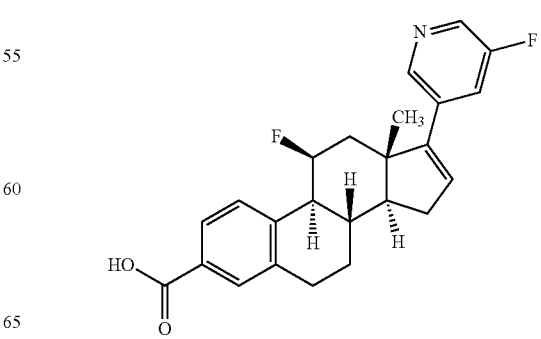

5 ml of methanol and 442 mg of lithium hydroxide monohydrate in 5 ml of water were added to a mixture of 862 mg (2.11 mmol) of methyl 11β-fluoro-17-(5-fluoropyridin-3-yl)estra-1,3,5(10),16-tetraene-3-carboxylate in 10 ml of THF, and the mixture was stirred at room temperature overnight. Water was added, and the reaction mixture was adjusted to pH=4 with 10% strength aqueous citric acid solution. The resulting precipitate was filtered off with suction, washed with ethyl acetate and dried. This gave 498 mg (60% of theory) of a white solid.

$^1$H-NMR (500 MHz, DMSO-d$_6$): δ [ppm]=1.19 (s, 3H), 1.44-1.59 (m, 1H), 1.80-1.96 (m, 2H), 1.96-2.08 (m, 2H), 2.18-2.29 (m, 1H), 2.32-2.42 (m, 1H), 2.59 (td, 1H), 2.74 (dd, 1H), 2.77 (br. s., 1H), 2.86-3.00 (m, 2H), 5.66-5.80 (m, 1H), 6.32 (dd, 1H), 7.48 (d, 1H), 7.65-7.78 (m, 3H), 8.47 (d, 1H), 8.54 (t, 1H).

EXAMPLE 1

4-[({[17-(5-Fluoropyridin-3-yl)estra-1,3,5(10),16-tetraen-3-yl]carbonyl}amino)methyl]-3,4,5,6-tetrahydro-2H-pyran-4-carboxylic acid

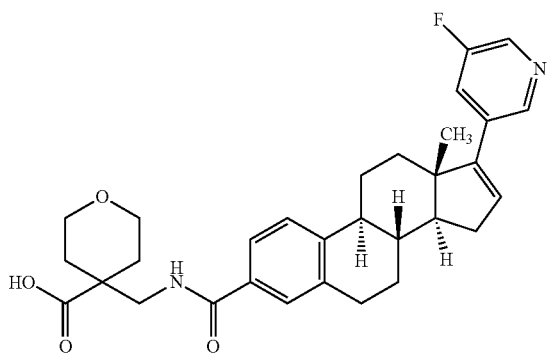

Step A: 100 mg (0.26 mmol) of 17-(5-fluoropyridin-3-yl)estra-1,3,5(10),16-tetraene-3-carboxylic acid were initially charged in 1 ml of DMF and 3 ml of THF. 119 mg (2.0 equiv.) of ethyl 4-(aminomethyl)-3,4,5,6-tetrahydro-2H-pyran-4-carboxylate hydrochloride, 41 mg (2.0 equiv.) of 1-hydroxy-1H-benzotriazole hydrate, 102 mg (2.0 equiv.) of 1-(3-dimethylaminopropyl)-3-ethylcarbodiimide hydrochloride and 0.11 ml of triethylamine were then added, and the mixture was stirred at RT overnight.

Step B: 0.66 ml of a 2M aqueous sodium hydroxide solution and 0.50 ml of methanol were then added, and the mixture was stirred at RT overnight. Water was added, and the reaction mixture was then acidified to a pH of 3-4 with a 10% strength aqueous citric acid solution. The aqueous phase was extracted three times with ethyl acetate, the combined org. phases were concentrated and the residue was purified by preparative HPLC (acetonitrile/water/formic acid). This gave 76 mg (55% of theory) of a solid.

$C_{31}H_{35}FN_2O_4$ (518.6). MS-ES+ mass found: 518.26.

$^1$H NMR (300 MHz, DMSO-d$_6$, selected signals) δ ppm 0.99 (s, 3H), 1.36-1.99 (m, 10H), 2.05-2.21 (m, 2H), 2.25-2.44 (m, 3H), 2.82-2.95 (m, 2H), 3.39 (d, 2H), 3.67-3.76 (m, 2H), 6.25-6.29 (m, 1H), 7.31 (d, 1H), 7.49-7.60 (m, 2H), 7.68 (dt, 1H), 8.27 (t, 1H), 8.43 (d, 1H), 8.49 (s, 1H), 12.5 (br. s).

EXAMPLE 2

N-{[17-(5-Fluoropyridin-3-yl)estra-1,3,5(10),16-tetraen-3-yl]carbonyl}-N-methyl-β-alanine

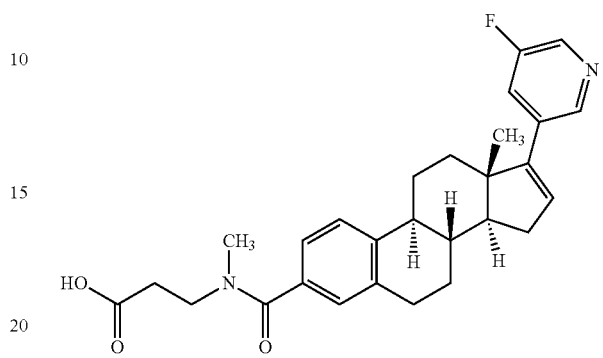

Step A: 1.62 g (1.0 equiv.) of 1-hydroxy-1H-benzotriazole hydrate, 4.06 g (2.0 equiv.) of 1-(3-dimethylaminopropyl)-3-ethylcarbodiimide hydrochloride (EDC) and 4.4 ml of triethylamine were added to a mixture of 4.00 g (10.6 mmol) of 17-(5-fluoropyridin-3-yl)estra-1,3,5(10),16-tetraene-3-carboxylic acid and 3.38 g (2 equiv.) of tert-butyl N-methyl-β-alaninate in 100 ml of THF and 5 ml of DMF, and the mixture was stirred at RT for 18 h. The mixture was diluted with water and extracted three times with ethyl acetate, and the extracts were washed with sodium chloride solution and concentrated. Purification of the residue with silica gel (hexane/ethyl acetate) gave 5.1 g of tert-butyl N-{[17-(5-fluoropyridin-3-yl)estra-1,3,5(10),16-tetraen-3-yl]carbonyl}-N-methyl-β-alaninate (93% of theory) as a solid.

Step B: 1.00 g (1.93 mmol) of tert-butyl N-{[17-(5-fluoropyridin-3-yl)estra-1,3,5(10),16-tetraen-3-yl]carbonyl}-N-methyl-β-alaninate was initially charged in 15 ml of dichloromethane, 1.5 ml of trifluoroacetic acid were added and the mixture was stirred at 40° C. overnight, poured into ice-water, stirred briefly and extracted three times with dichloromethane. The combined organic phases were washed with saturated sodium chloride solution, filtered through a water-repelling filter and concentrated. Diethyl ether was added to the crude product, the mixture was stirred and filtered off with suction and the product was washed with diethyl ether and dried. This gave 0.79 g (89% of theory) of N-{[17-(5-fluoropyridin-3-yl)estra-1,3,5 (10),16-tetraen-3-yl]carbonyl}-N-methyl-β-alanine.

$C_{28}H_{31}FN_2O_3$ (462.6). MS-ES+ mass found: 462.23.

$^1$H-NMR (300 MHz, DMSO-d6): δ [ppm]=1.00 (s, 3H), 1.33-1.79 (m, 5H), 1.82-1.99 (m, 1H), 2.08-2.21 (m, 2H), 2.21-2.43 (m, 3H), 2.50 (s), 2.74-2.88 (5H, contains s at 2.88 ppm), 3.36-3.71 (m), 6.27 (s., 1H), 6.99-7.16 (m, 2H), 7.28 (d, 1H), 7.68 (dt, 1H), 8.43 (d, 1H), 8.49 (s, 1H), 8.48-8.56 (m, 1H), 12.28 (br. s.).

EXAMPLE 3

1-[({[17-(5-Fluoropyridin-3-yl)estra-1,3,5(10),16-tetraen-3-yl]carbonyl}amino)methyl]-cyclopropane-1-carboxylic acid

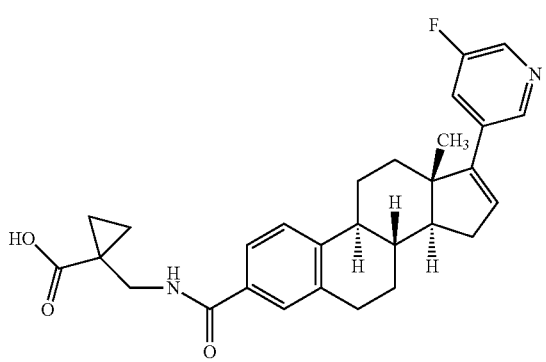

Analogously to Example 1, 100 mg (0.26 mmol) of 17-(5-fluoropyridin-3-yl)estra-1,3,5(10),16-tetraene-3-carboxylic acid and 88 mg (2.0 equiv.) of methyl 1-(aminomethyl)cyclopropane-1-carboxylate hydrochloride were converted into 72 mg (57% of theory) of the title compound.

$C_{29}H_{31}FN_2O_3$ (474.6). MS-ES+ mass found: 474.23.

$^1$H-NMR (300 MHz, DMSO-d6): δ [ppm]=0.82-0.90 (m, 2H), 0.95-1.06 (m, 5H), 1.33-1.81 (m, 5H), 1.56 (d, 3H), 1.84-1.97 (m, 1H), 1.84-1.97 (m, 1H), 2.05-2.44 (m), 2.80-2.94 (m, 2H), 3.44-3.54 (m, 2H), 6.27 (s., 1H), 7.31 (d, 1H), 7.50-7.60 (m, 2H), 7.68 (dt, 1H), 8.18 (t, 1H), 8.43 (d, 1H), 8.49 (s, 1H), 12.3 (s, 1H).

EXAMPLE 4

1-[({[17-(5-Fluoropyridin-3-yl)estra-1,3,5(10),16-tetraen-3-yl]carbonyl}amino)methyl]-cyclopentane-1-carboxylic acid

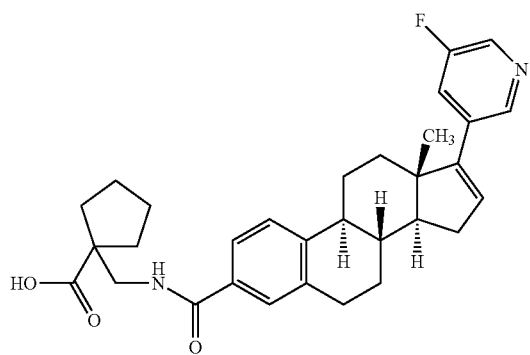

Analogously to Example 1 (step B was carried out at 50° C. overnight and after addition of a further 5 equiv. of 2M aqueous sodium hydroxide solution by stirring at 60° C. overnight), 100 mg (0.26 mmol) of 17-(5-fluoropyridin-3-yl)estra-1,3,5(10),16-tetraene-3-carboxylic acid and 103 mg (2.0 equiv.) of methyl 1-(aminomethyl)cyclopentane-1-carboxylate hydrochloride were converted into 63 mg (48% of theory) of the title compound.

$C_{31}H_{35}FN_2O_3$ (502.6). MS-ES+ mass found: 502.26.

$^1$H-NMR (400 MHz, DMSO-d6): δ [ppm]=0.99 (s, 3H), 1.36-1.66 (m), 1.73 (td, 1H), 1.81-1.95 (m, 3H), 2.07-2.20 (m, 2H), 2.25-2.44 (m), 2.83-2.95 (m, 2H), 3.45 (d, 2H), 6.25-6.29 (m, 1H), 7.31 (d, 1H), 7.49-7.56 (m, 2H), 7.69 (dt, 1H), 8.14 (t, 1H), 8.43 (d, 1H), 8.49 (s, 1H), 12.2 (s).

EXAMPLE 5

3-({[17-(5-Fluoropyridin-3-yl)estra-1,3,5(10),16-tetraen-3-yl]carbonyl}amino)-2,2-dimethylpropanoic acid

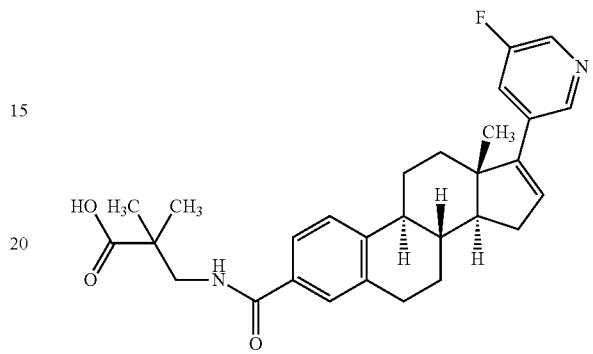

Analogously to Example 1 (step B was carried out at 50° C. overnight and after addition of a further 5 equiv. of 2M aqueous sodium hydroxide solution while stirring at 60° C. overnight), 100 mg (0.26 mmol) of 17-(5-fluoropyridin-3-yl)estra-1,3,5(10),16-tetraene-3-carboxylic acid and 89 mg (2.0 equiv.) of methyl 3-amino-2,2-dimethylpropanoate hydrochloride were converted into 63 mg (50% of theory) of the title compound.

$C_{29}H_{33}FN_2O_3$ (476.6). MS-ES+ mass found: 476.25.

$^1$H-NMR (400 MHz, DMSO-d6): δ [ppm]=0.99 (s, 3H), 1.06 (s, 6H), 1.36-1.66 (m, 4H), 1.73 (td, 1H), 1.86-1.95 (m, 1H), 2.07-2.20 (m, 2H), 2.25-2.45 (m, 3H), 2.84-2.92 (m, 2H), 3.37 (d, superimposed by water signal), 6.25-6.29 (m, 1H), 7.31 (d, 1H), 7.50-7.57 (m, 2H), 7.69 (dt, 1H), 8.15 (t, 1H), 8.43 (d, 1H), 8.49 (t, 1H), 12.2 (s).

EXAMPLE 6

1-{[17-(5-Fluoropyridin-3-yl)estra-1,3,5(10),16-tetraen-3-yl]carbonyl}piperidine-4-carboxylic acid

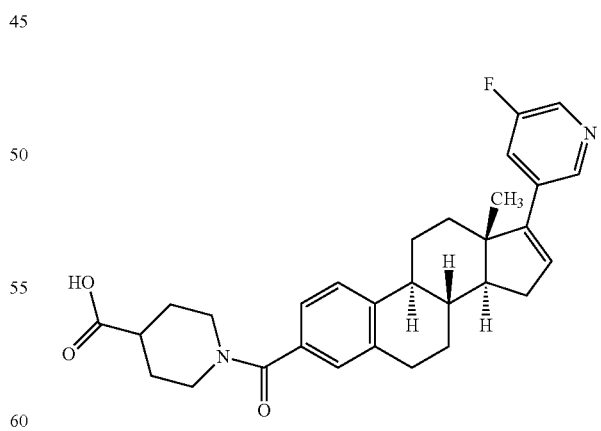

Analogously to Example 1 (step B was carried out at 50° C. over a period of 5 h), 100 mg (0.26 mmol) of 17-(5-fluoropyridin-3-yl)estra-1,3,5(10),16-tetraene-3-carboxylic acid and 83 mg (2.0 equiv.) of ethyl piperidine-4-carboxylate were converted into 65 mg (50% of theory) of the title compound.

$C_{30}H_{33}FN_2O_3$ (488.6). MS-ES+ mass found: 488.25.

$^1$H-NMR (400 MHz, DMSO-d$_6$): δ [ppm]=1.00 (s, 3H), 1.33-1.96 (m, 10H), 2.03-2.22 (m, 2H), 2.24-2.43 (m, 3H), 2.79-2.94 (m, 3H), 3.02 (br. s., 1H), 3.57 (br. s., 1H), 4.26 (br. s., 1H), 6.25-6.29 (m, 1H), 7.00-7.11 (m, 2H), 7.29 (d, 1H), 7.69 (dt, 1H), 8.43 (d, 1H), 8.47-8.51 (m, 1H), 12.3 (s).

EXAMPLE 7

N-{[17-(5-Fluoropyridin-3-yl)estra-1,3,5(10),16-tetraen-3-yl]carbonyl}-2-methylalanine

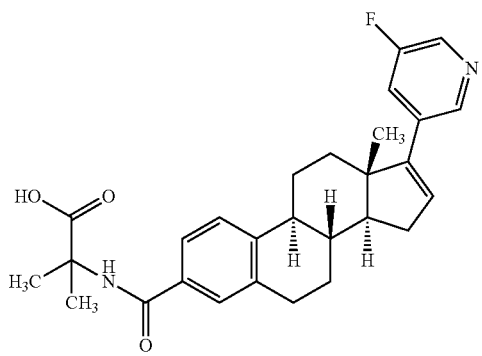

Analogously to Example 1 (step B was carried out by heating at 50° C. overnight and, after addition of a further 5 equiv. of 2M aqueous sodium hydroxide solution, stirring at 60° C. overnight), 100 mg (0.26 mmol) of 17-(5-fluoropyridin-3-yl)estra-1,3,5(10),16-tetraene-3-carboxylic acid and 81 mg (2.0 equiv.) of methyl 3-amino-2,2-dimethylpropanoate hydrochloride were converted into 81 mg (66% of theory) of the title compound.

$C_{28}H_{31}FN_2O_3$ (462.6). MS-ES+ mass found: 462.23.

$^1$H-NMR (300 MHz, DMSO-d6): δ [ppm]=0.99 (s, 3H), 1.39 (s, 6H), 1.4-1.82 (m), 1.86-1.98 (m, 1H), 2.05-2.43 (m, 2H), 2.20-2.50 (m), 2.83-2.94 (m, 2H), 6.27 (s, 1H), 7.31 (d, 1H), 7.52-7.61 (m, 2H), 7.65-7.72 (m, 1H), 8.29 (s, 1H), 8.43 (d, 1H), 8.46-8.53 (m, 1H), 12.1 (s).

EXAMPLE 8

4-({[17-(5-Fluoropyridin-3-yl)estra-1,3,5(10),16-tetraen-3-yl]carbonyl}amino)butanoic acid

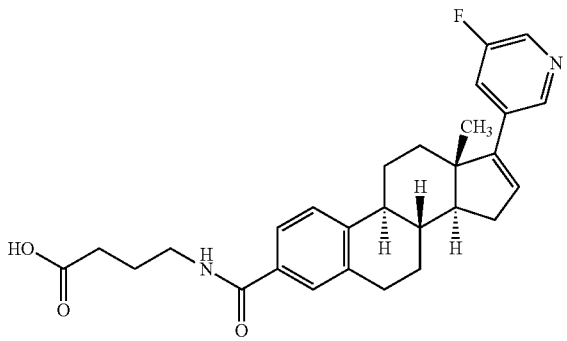

Analogously to Example 1, 100 mg (0.26 mmol) of 17-(5-fluoropyridin-3-yl)estra- 1,3,5(10),16-tetraene-3-carboxylic acid and 81 mg (2.0 equiv.) of methyl 4-aminobutanoate hydrochloride were converted into 58 mg (48% of theory) of the title compound.

$C_{28}H_{31}FN_2O_3$ (462.6). MS-ES+ mass found: 462.23.

$^1$H-NMR (300 MHz, DMSO-d6): δ [ppm]=0.99 (s, 3H), 1.39-1.78 (m, 7H), 1.83-1.99 (m, 1H), 2.05-2.50 (m, superimposed by DMSO signal), 3.1-3.4 (m, superimposed by water signal), 2.79-2.98 (m, 2H), 6.26 (s., 1H), 7.31 (d, 1H), 7.52-7.59 (m, 2H), 7.67 (dt, 1H), 8.32 (t, 1H), 8.43 (d, 1H), 8.49 (s, 1H), 12.0 (s).

EXAMPLE 9

N-{[17-(5-Fluoropyridin-3-yl)estra-1,3,5(10),16-tetraen-3-yl]carbonyl}-β-alanine

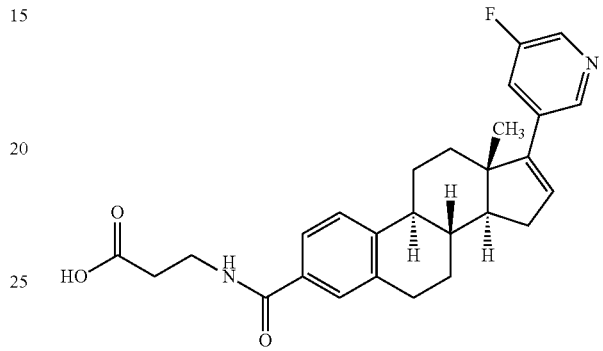

Analogously to Example 1, 100 mg (0.26 mmol) of 17-(5-fluoropyridin-3-yl)estra-1,3,5(10),16-tetraene-3-carboxylic acid and 81 mg (2.0 equiv.) of ethyl β-alaninate hydrochloride were converted into 59 mg (50% of theory) of the title compound.

$C_{27}H_{29}FN_2O_3$ (448.5). MS-ES+ mass found: 448.22.

$^1$H-NMR (300 MHz, DMSO-d6): δ [ppm]=0.99 (s, 3H), 1.38-1.78 (m, 5H), 1.83-1.98 (m, 1H), 2.05-2.21 (m, 2H), 2.25-2.44 (m, superimposed by DMSO signal), 2.80-2.94 (m, 2H), 3.35-3.51 (m, superimposed by water signal), 6.26 (s., 1H), 7.31 (d, 1H), 7.50-7.58 (m, 2H), 7.62-7.74 (m, 1H), 8.36 (t, 1H), 8.43 (d, 1H), 8.49 (s, 1H), 12.2 (s).

EXAMPLE 10

N-{[17-(5-Fluoropyridin-3-yl)estra-1,3,5(10),16-tetraen-3-yl]carbonyl}glycine

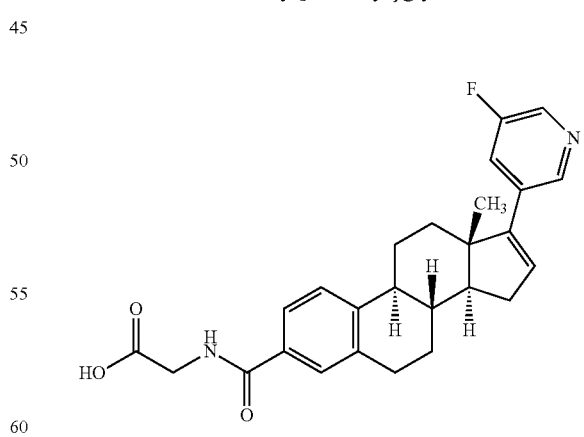

Analogously to Example 1, 100 mg (0.26 mmol) of 17-(5-fluoropyridin-3-yl)estra-1,3,5(10),16-tetraene-3-carboxylic acid and 67 mg (2.0 equiv.) of methyl glycinate hydrochloride were converted into 58 mg (50% of theory) of the title compound.

$C_{26}H_{27}FN_2O_3$ (434.5). MS-ES+ mass found: 434.20.

¹H-NMR (400 MHz, DMSO-d₆): δ [ppm]=1.00 (s, 3H), 1.37-1.67 (m, 4H), 1.74 (td, 1H), 1.85-1.97 (m, 1H), 2.07-2.21 (m, 2H), 2.26-2.5 (m, superimposed by DMSO signal), 2.84-2.94 (m, 2H), 3.86 (d, 2H), 6.25-6.29 (m, 1H), 7.34 (d, 1H), 7.55-7.61 (m, 2H), 7.64-7.72 (m, 1H), 8.43 (d, 1H), 8.49 (t, 1H), 8.64 (t, 1H), 12.5 (s).

EXAMPLE 11

(1R*,2S*)-2-({[17-(5-Fluoropyridin-3-yl)estra-1,3,5(10),16-tetraen-3-yl]carbonyl}amino)-cyclopentane-1-carboxylic acid

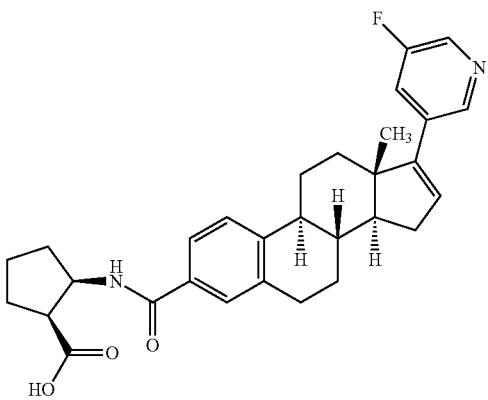

Analogously to Example 1, 100 mg (0.26 mmol) of 17-(5-fluoropyridin-3-yl)estra-1,3,5(10),16-tetraene-3-carboxylic acid and 103 mg (2.0 equiv.) of (1R*,2S*)-ethyl 2-aminocyclopentane-1-carboxylate hydrochloride were converted into 63 mg (49% of theory) of the title compound.

$C_{30}H_{33}FN_2O_3$ (488.6). MS-ES+ mass found: 488.25.

¹H-NMR (300 MHz, DMSO-d₆): δ [ppm]=1.00 (s, 3H), 1.39-1.66 (m, 5H), 1.68-1.96 (m, 7H), 2.02-2.21 (m, 2H), 2.24-2.41 (m), 2.78-2.98 (m, 3H), 4.42-4.57 (m, 1H), 6.27 (s., 1H), 7.30 (d, 1H), 7.46-7.58 (m, 2H), 7.68 (dt, 1H), 8.03 (d, 1H), 8.43 (d, 1H), 8.46-8.52 (m, 1H), 11.9 (s).

EXAMPLE 12

(S)-3-({[17-(5-Fluoropyridin-3-yl)estra-1,3,5(10),16-tetraen-3-yl]carbonyl}amino)-butanoic acid

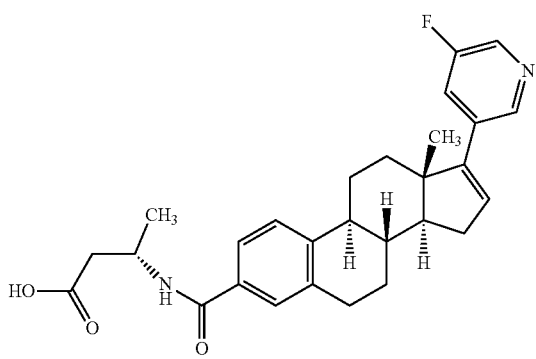

Analogously to Example 1 (in step B, an additional 5 equiv. of 2M aqueous sodium hydroxide solution were added, the mixture was stirred for 4 h, another 5 equiv. of 2M aqueous sodium hydroxide solution were added, the mixture was stirred in a microwave oven at 110° C./300 Watt for 30 min, 10 equiv. of 2M aqueous sodium hydroxide solution were added and the mixture was then heated in a microwave oven at 120° C./300 Watt for 60 min and at 130° C./300 Watt for 60 min), 100 mg (0.26 mmol) of 17-(5-fluoropyridin-3-yl)estra-1,3,5(10),16-tetraene-3-carboxylic acid and 84 mg of tert-butyl (S)-3-aminobutyrate were converted into 24 mg (20% of theory) of the title compound.

$C_{28}H_{31}FN_2O_3$ (462.6). MS-ES+ mass found: 462.23.

¹H-NMR (400 MHz, DMSO-d₆): δ [ppm]=1.02 (s, 3H), 1.16 (d, 3H), 1.38-1.68 (m, 4H), 1.76 (td, 1H), 1.87-2.01 (m, 1H), 2.09-2.24 (m, 2H), 2.27-2.46 (m, 4H), 2.51-2.61 (m, 1H), 2.82-3.00 (m, 2H), 4.31 (spt, 1H), 6.27-6.31 (m, 1H), 7.34 (d, 1H), 7.50-7.61 (m, 2H), 7.70 (dt, 1H), 8.16 (d, 1H), 8.46 (d, 1H), 8.50-8.54 (m, 1H), 12.2 (br. s., 1H).

EXAMPLE 13

(R)-3-({[17-(5-Fluoropyridin-3-yl)estra-1,3,5(10),16-tetraen-3-yl]carbonyl}amino)-butanoic acid

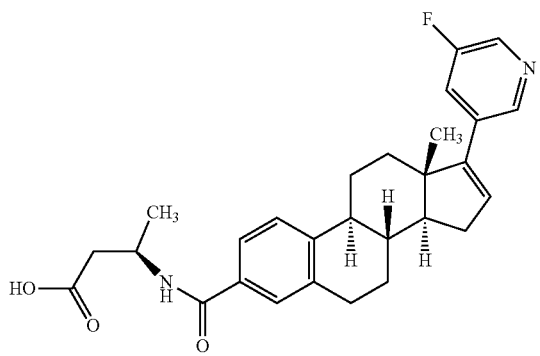

Analogously to Example 1 (in step B, an additional 5 equivalents of 2M aqueous sodium hydroxide solution were added and the mixture was stirred at 50° C. for 30 h), 100 mg (0.26 mmol) of 17-(5-fluoropyridin-3-yl)estra-1,3,5(10),16-tetraene-3-carboxylic acid and 84 mg of tert-butyl (R)-3-aminobutyrate were converted into 34 mg (28% of theory) of the title compound.

$C_{28}H_{31}FN_2O_3$ (462.6). MS-ES+ mass found: 462.23.

¹H-NMR (400 MHz, DMSO-d₆): δ [ppm]=1.02 (s, 3H), 1.16 (d, 3H), 1.39-1.69 (m, 4H), 1.76 (td, 1H), 1.88-2.00 (m, 1H), 2.09-2.23 (m, 2H), 2.27-2.47 (m, 4H), 2.51-2.61 (m, 1H), 2.82-2.98 (m, 2H), 4.32 (spt, 1H), 6.24-6.34 (m, 1H), 7.34 (d, 1H), 7.52-7.60 (m, 2H), 7.70 (dt, 1H), 8.15 (d, 1H), 8.46 (d, 1H), 8.50-8.54 (m, 1H), 12.1 (br. s., 1H).

EXAMPLE 14

3-({[17-(5-Methoxypyridin-3-yl)estra-1,3,5(10),16-tetraen-3-yl]carbonyl}amino)-2,2-dimethylpropanoic acid

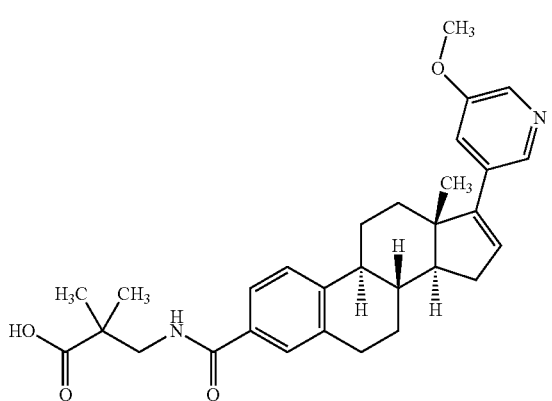

Analogously to Example 1 (step B was carried out by stirring at 50° C. for 7 h), 100 mg (0.26 mmol) of 17-(5-methoxypyridin-3-yl)estra-1,3,5(10),16-tetraene-3-carboxylic acid and 75 mg (0.51 mmol) of ethyl 3-amino-2,2-dimethylpropanoate were converted into 12 mg (10% of theory) of the title compound.

$C_{30}H_{36}N_2O_4$ (488.63). MS-ES+ mass found: 488.27.

$^1$H-NMR (300 MHz, DMSO-d6): δ [ppm]=0.98 (s, 3H), 1.06 (s, 6H), 1.31-1.82 (m, 5H), 1.84-1.97 (m, 1H), 2.00-2.19 (m, 2H), 2.20-2.40 (m), 2.80-2.95 (m, 2H), 3.36-3.38 (m, partially obscured by water signal), 3.81 (s, 3H), 6.16 (s., 1H), 7.20-7.37 (m, 2H), 7.46-7.63 (m, 2H), 8.09-8.27 (m, 3H).

EXAMPLE 15

N-{[17-(5-Methoxypyridin-3-yl)estra-1,3,5(10),16-tetraen-3-yl]carbonyl}-β-alanine

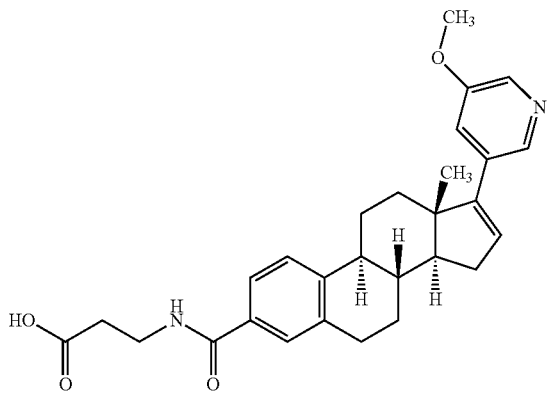

Analogously to Example 1 (step B was carried out by stirring at 50° C. for 7 h), 100 mg (0.26 mmol) of 17-(5-methoxypyridin-3-yl)estra-1,3,5(10),16-tetraene-3-carboxylic acid and 79 mg (0.51 mmol) of ethyl β-alaninate hydrochloride were converted into 64 mg (54% of theory) of the title compound.

$C_{28}H_{32}N_2O_4$ (460.58). MS-ES+ mass found: 460.24.

$^1$H-NMR (300 MHz, DMSO-d$_6$): δ [ppm]=0.98 (s, 3H), 1.38-1.78 (m, 5H), 1.85-1.96 (m, 1H), 2.04-2.18 (m, 2H), 2.21-2.41 (m, 3H), 2.76-2.98 (m, 2H), 3.34-3.50 (m, 2H), 3.81 (s, 3H), 6.14-6.18 (m, 1H), 7.23-7.28 (m, 1H), 7.31 (d, 1H), 7.46-7.63 (m, 2H), 8.16 (d, 1H), 8.20 (d, 1H), 8.38 (t, 1H), 12.2 (br. s., 1H).

EXAMPLE 16

N-{[17-(5-Methoxypyridin-3-yl)estra-1,3,5(10),16-tetraen-3-yl]carbonyl}-N-methyl-β-alanine

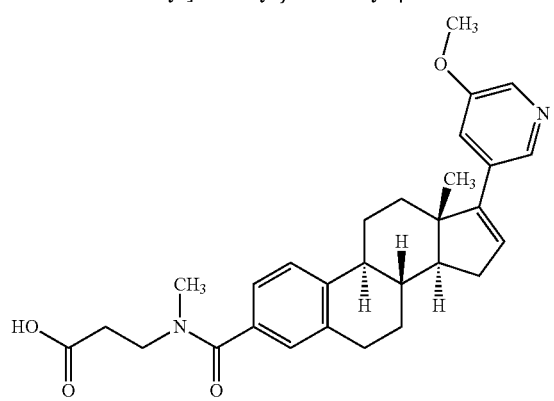

39 mg (1.0 equiv.) of 1-hydroxy-1H-benzotriazole hydrate, 98 mg (2.0 equiv.) of 1-[3-(dimethylamino)propyl]-3-ethylcarbodiimide hydrochloride and 0.11 ml of triethylamine were added to a mixture of 100 mg (0.26 mmol) of 17-(5-methoxypyridin-3-yl)estra-1,3,5(10),16-tetraene-3-carboxylic acid and 82 mg (2 equiv.) of tert-butyl N-methyl-β-alaninate in 3 ml of THF and 1 ml of DMF, and the mixture was stirred at RT for 72 h. The mixture was diluted with water and extracted three times with ethyl acetate, and the extracts were concentrated. 4 ml of dichloromethane and 1 ml of trifluoroacetic acid were added to the residue, and the mixture was stirred at room temperature for 17 h. The mixture was concentrated giving, after purification of the residue by preparative HPLC, 66 mg of the title compound.

$C_{29}H_{34}N_2O_4$. (474.61). MS-ES+ mass found: 474.25.

$^1$H-NMR (300 MHz, DMSO-d$_6$): δ [ppm]=0.99 (s, 3H), 1.38-1.78 (m, 5H), 1.82-1.96 (m, 1H), 2.03-2.18 (m, 2H), 2.21-2.43 (m, 3H), 2.79-2.93 (m, 5H), 3.42 (br. s., 1H), 3.57 (br. s., 1H), 3.81 (s, 3H), 6.16 (s, 1H), 6.99-7.14 (m, 2H), 7.23-7.31 (m, 2H), 8.13-8.22 (m, 2H), 12.3 (br. s., 1H).

EXAMPLE 17

N-{[17-(Pyrimidin-5-yl)estra-1,3,5(10),16-tetraen-3-yl]carbonyl}-β-alanine

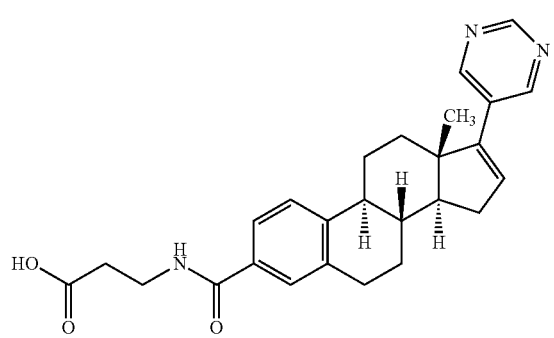

Analogously to Example 1 (step B was carried out by stirring at 50° C. for 18 h), 100 mg (0.28 mmol) of 17-(pyrimidin-5-yl)estra-1,3,5(10),16-tetraene-3-carboxylic acid and 85 mg (2.0 equiv.) of ethyl β-alaninate hydrochloride were converted into 63 mg (50% of theory) of the title compound.

$C_{26}H_{29}N_3O_3$ (431.5). MS-ES+ mass found: 431.22.

$^1$H-NMR (300 MHz, DMSO-$d_6$): δ [ppm]=0.99 (s, 3H), 1.36-1.79 (m, 5H), 1.84-1.97 (m, 1H), 2.06-2.20 (m, 2H), 2.25-2.41 (m, 4H), 2.82-2.93 (m, 2H), 3.35-3.45 (m, 2H), 6.28-6.33 (m, 1H), 7.31 (d, 1H), 7.50-7.58 (m, 2H), 8.38 (t, 1H), 8.83 (s, 2H), 9.04 (s, 1H), 12.19 (br. s., 1H).

EXAMPLE 18

4-({[17-(Pyrimidin-5-yl)estra-1,3,5(10),16-tetraen-3-yl]carbonyl}amino)butanoic acid

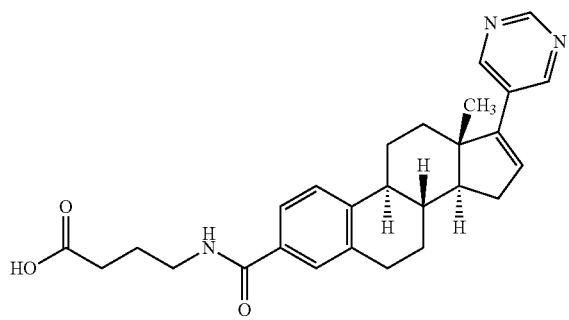

Analogously to Example 1 (step B was carried out by stirring at 50° C. for 18 h), 100 mg (0.28 mmol) of 17-(pyrimidin-5-yl)estra-1,3,5(10),16-tetraene-3-carboxylic acid and 85 mg (2.0 equiv.) of methyl 4-aminobutanoate hydrochloride were converted into 61 mg (47% of theory) of the title compound.

$C_{27}H_{31}N_3O_3$ (445.6). MS-ES+ mass found: 445.24.

$^1$H-NMR (300 MHz, DMSO-$d_6$): δ [ppm]=0.99 (s, 3H), 1.39-1.79 (m, 7H), 1.85-1.98 (m, 1H), 2.05-2.26 (m, 4H), 2.26-2.41 (m, 3H), 2.81-2.95 (m, 2H), 3.15-3.25 (m, 2H), 6.27-6.34 (m, 1H), 7.31 (d, 1H), 7.50-7.61 (m, 2H), 8.34 (t, 1H), 8.83 (s, 2H), 9.04 (s, 1H), 12.04 (br. s., 1H).

EXAMPLE 19

N-Methyl-N-{[17-(pyrimidin-5-yl)estra-1,3,5(10),16-tetraen-3-yl]carbonyl}-β-alanine

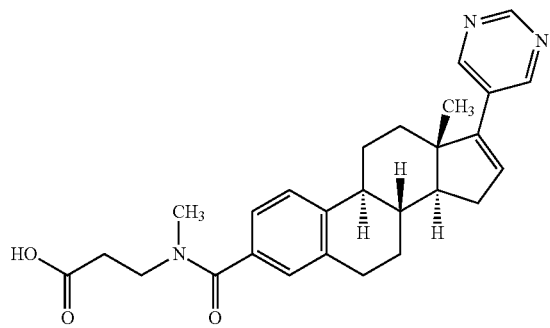

42 mg (1 equiv.) of 1-hydroxy-1H-benzotriazole hydrate, 106 mg (2.0 equiv.) of 1-[3-(dimethylamino)propyl]-3-ethylcarbodiimide hydrochloride and 0.12 ml of triethylamine were added to a mixture of 100 mg (0.26 mmol) of 17-(pyrimidin-5-yl)estra-1,3,5(10),16-tetraene-3-carboxylic acid and 88 mg (2 equiv.) of tert-butyl N-methyl-β-alaninate in 3 ml of THF and 1 ml of DMF, and the mixture was stirred at RT for 72 h. The mixture was diluted with water and extracted three times with ethyl acetate, and the extracts were concentrated. 3 ml of dichloromethane and 1 ml of trifluoroacetic acid were added to the residue, and the mixture was stirred at room temperature for 72 h. The mixture was concentrated giving, after purification of the residue by preparative HPLC, 56 mg of the title compound.

$C_{27}H_{31}N_3O_3$ (445.6). MS-ES+ mass found: 445.24.

$^1$H-NMR (300 MHz, DMSO-$d_6$): δ [ppm]=1.00 (s, 3H), 1.36-1.77 (m, 5H), 1.85-1.94 (m, 1H), 2.07-2.20 (m, 2H), 2.26-2.5 (m, obscured), 2.80-2.92 (m, 5H), 3.42 (br. s., 1H), 3.57 (br. s., 1H), 6.27-6.33 (m, 1H), 7.02-7.11 (m, 2H), 7.29 (d, 1H), 8.83 (s, 2H), 9.04 (s, 1H), 12.3 (br. s, 1H).

EXAMPLE 20

2,2-Dimethyl-3-({[17-(pyrimidin-5-yl)estra-1,3,5(10),16-tetraen-3-yl]carbonyl}amino)-propanoic acid

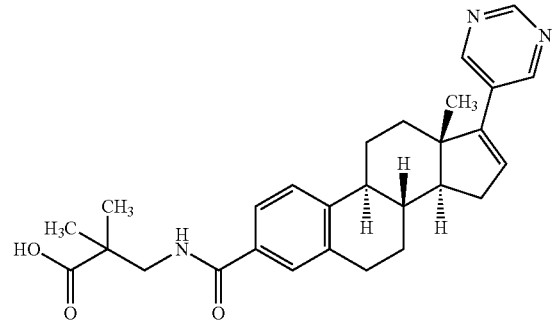

Analogously to Example 1 (step B was carried out by stirring at 50° C. for 5 h), 100 mg (0.28 mmol) of 17-(pyrimidin-5-yl)estra-1,3,5(10),16-tetraene-3-carboxylic acid and 81 mg (0.55 mmol) of ethyl 3-amino-2,2-dimethylpropanoate were converted into 10 mg (8% of theory) of the title compound.

$C_{28}H_{33}N_3O_3$ (459.6). MS-ES+ mass found: 459.25.

$^1$H-NMR (600 MHz, DMSO-$d_6$): δ [ppm]=1.02 (s, 3H), 1.09 (s, 6H), 1.42-1.50 (m, 1H), 1.53-1.68 (m, 3H), 1.77 (td, 1H), 1.91-1.97 (m, 1H), 2.13-2.20 (m, 2H), 2.31-2.39 (m, 2H), 2.41-2.47 (m, 1H), 2.89-2.94 (m, 2H), 3.40 (d, 2H), 6.33 (dd, 1H), 7.34 (d, 1H), 7.53-7.59 (m, 2H), 8.16-8.21 (m., 1H), 8.85 (s, 2H), 9.07 (s, 1H), 12.25 (br. s., 1H).

EXAMPLE 21

N-({17-[5-(Trifluoromethyl)pyridin-3-yl]estra-1,3,5(10),16-tetraen-3-yl}carbonyl)-β-alanine

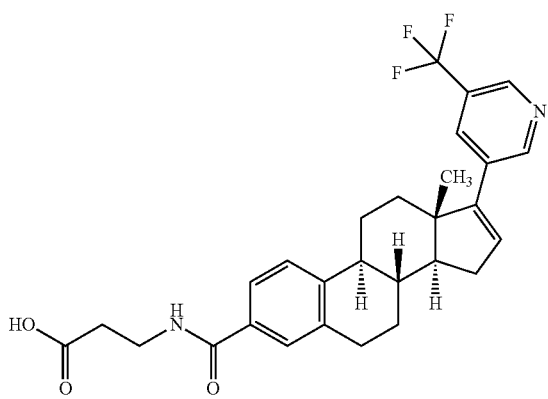

Analogously to Example 1 (step B was carried out by stirring at 50° C. for 18 h), 100 mg (0.23 mmol) of 17-[5-(trifluoromethyl)pyridin-3-yl]estra-1,3,5(10),16-tetraene-3-carboxylic acid and 72 mg (2.0 equiv.) of ethyl β-alaninate hydrochloride were converted into 65 mg (56% of theory) of the title compound.

$C_{28}H_{29}F_3N_2O_3$ (498.6). MS-ES+ mass found: 498.21.

$^1$H-NMR (300 MHz, DMSO-$d_6$): δ [ppm]=1.01 (s, 3H), 1.35-1.69 (m, 4H), 1.76 (td, 1H), 1.84-2.00 (m, 1H), 2.03-2.21 (m, 2H), 2.24-2.41 (m,), 2.78-2.96 (m, 2H), 3.35-3.53 (m, 2H), 6.33-6.38 (m, 1H), 7.31 (d, 1H), 7.47-7.62 (m, 2H), 8.03 (s, 1H), 8.35 (t, 1H), 8.78-8.86 (m, 1H), 8.86-8.97 (m, 1H), 12.2 (br. s., 1H).

EXAMPLE 22

N-Methyl-N-({17-[5-(trifluoromethyl)pyridin-3-yl]estra-1,3,5(10),16-tetraen-3-yl}carbonyl)-β-alanine

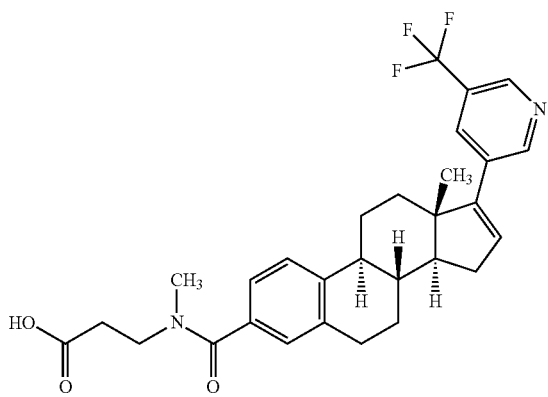

Step A: 36 mg (1 equiv.) of 1-hydroxy-1H-benzotriazole hydrate, 90 mg (2.0 equiv.) of 1-[3-(dimethylamino)propyl]-3-ethylcarbodiimide hydrochloride and 98 microliters of triethylamine were added to a mixture of 100 mg (0.23 mmol) of 17-[5-(trifluoromethyl)pyridin-3-yl]estra-1,3,5(10),16-tetraene-3-carboxylic acid and 74 mg (2 equiv.) of tert-butyl N-methyl-β-alaninate in 3 ml of THF, and the mixture was stirred at RT for 4 h. The mixture was diluted with water and extracted three times with ethyl acetate, and the extracts were concentrated.

Step B: 2 ml of dichloromethane and 180 microliters of trifluoroacetic acid were added, and the mixture was stirred at a bath temperature of 40° C. for 18 h. A further 90 microliters of trifluoroacetic acid were added, and the mixture was stirred at 40° C. for 5 h. Water was added, the phases were separated and the aqueous phase was extracted twice with dichloromethane. The organic phases were concentrated and the residue was purified by HPLC (acetonitrile/water/formic acid). This gave 83 mg (69% of theory) of the title compound.

$C_{29}H_{31}F_3N_2O_3$ (512.58). MS-ES+ mass found: 512.23.

$^1$H-NMR (300 MHz, DMSO-$d_6$): δ [ppm]=1.01 (s, 3H), 1.36-1.51 (m, 1H), 1.52-1.81 (m, 4H), 1.84-1.98 (m, 1H), 2.04-2.21 (m, 2H), 2.25-2.40 (m,), 2.79-2.96 (m, 5H), 3.42 (br. s.), 3.55 (br. s.), 6.35 (s, 1H), 7.00-7.15 (m, 2H), 7.28 (d, 1H), 8.03 (s, 1H), 8.81-8.87 (m, 1H), 8.87-8.95 (m, 1H), 12.3 (br. s., 1H).

EXAMPLE 23

N-{[17-(5-Fluoropyridin-3-yl)estra-1,3,5(10),16-tetraen-3-yl]carbonyl}-L-proline

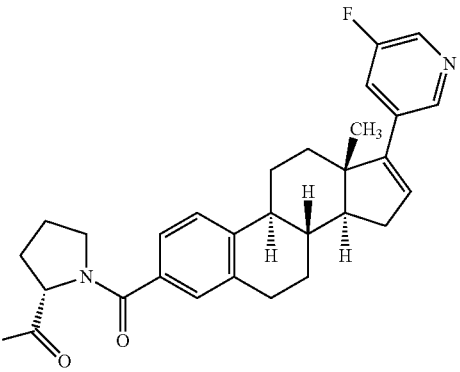

Analogously to Example 22, 100 mg (0.26 mmol) of 17-(5-fluoropyridin-3-yl)estra-1,3,5(10),16-tetraene-3-carboxylic acid were reacted with 91 mg (2.0 equiv.) of tert-butyl L-prolinate. Purification by preparative HPLC gave 65 mg (50% of theory) of the title compound.

$C_{29}H_{31}FN_2O_3$ (474.6). MS-ES+ mass found: 474.23.

$^1$H-NMR (300 MHz, DMSO-$d_6$): δ [ppm]=1.00 (s, 3H), 1.39-1.94 (m,), 2.05-2.43 (m,), 2.77-2.94 (m, 2H), 3.40-3.59 (m, 2H), 4.27-4.40 (m, 1H), 6.27 (s., 1H), 7.04-7.34 (m, 3H), 7.64-7.73 (m, 1H), 8.43 (d, 1H), 8.49 (s, 1H), 12.5 (br. s., 1H).

The title compound was analysed by analytical HPLC:

| | |
|---|---|
| System: | Waters: Alliance 2695, DAD 996 |
| Column: | Chiralpak AS-RH 5 μm 150 × 4.6 mm |
| Solvent: | $H_2O$ (0.1% by volume formic acid)/acetonitrile 50:50 (v/v) |
| Flow rate: | 1.0 ml/min |
| Temperature: | 25° C. |
| Solution: | 1.0 mg/ml ethanol/methanol 2:1 |
| Injection: | 5.0 μl |
| Detection: | DAD 254 nm |
| Peak | Rt in min |
| 1 | 8.15 |

EXAMPLE 24

N-{[17-(5-Fluoropyridin-3-yl)estra-1,3,5(10),16-tetraen-3-yl]carbonyl}-D-proline

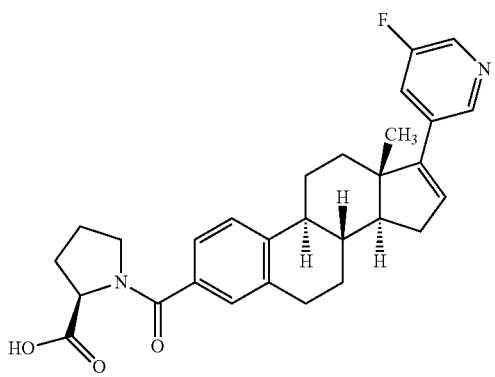

Analogously to Example 22, 100 mg (0.26 mmol) of 17-(5-fluoropyridin-3-yl)estra-1,3,5(10),16-tetraene-3-carboxylic acid were reacted with 91 mg (2.0 equiv.) of tert-butyl D-prolinate. Purification by preparative HPLC gave 66 mg (52% of theory) of the title compound.

$C_{29}H_{31}FN_2O_3$ (474.6). MS-ES+ mass found: 474.23.

$^1$H-NMR (300 MHz, DMSO-$d_6$): δ [ppm]=1.00 (s, 3H), 1.34-1.97 (m), 2.05-2.43 (m), 2.75-2.94 (m, 2H), 3.42-3.59 (m, 2H), 4.25-4.40 (m, 1H), 6.27 (s., 1H), 7.02-7.36 (m, 3H), 7.68 (d, 1H), 8.43 (d, 1H), 8.49 (s, 1H), 12.5 (br. s., 1H).

The title compound was analysed by analytical HPLC:

| | |
|---|---|
| System: | Waters: Alliance 2695, DAD 996 |
| Column: | Chiralpak AS-RH 5 μm 150 × 4.6 mm |
| Solvent: | H$_2$O (0.1% by volume formic acid)/acetonitrile 50:50 (v/v) |
| Flow rate: | 1.0 ml/min |
| Temperature: | 25° C. |
| Solution: | 1.0 mg/ml ethanol/methanol 2:1 |
| Injection: | 5.0 μl |
| Detection: | DAD 254 nm |
| Peak | Rt in min |
| 2 | 9.50 |

EXAMPLE 25

4-({[11β-Fluoro-17-(5-fluoropyridin-3-yl)estra-1,3,5(10),16-tetraen-3-yl]carbonyl}-amino)butanoic acid

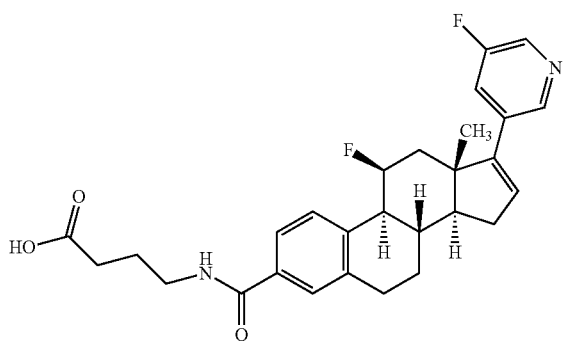

Analogously to Example 1, 100 mg of 11β-fluoro-17-(5-fluoropyridin-3-yl)estra-1,3,5(10),16-tetraene-3-carboxylic acid and 78 mg (2.0 equiv.) of methyl 4-aminobutanoate hydrochloride were converted into 80 mg (66% of theory) of the title compound.

$C_{28}H_{30}F_2N_2O_3$ (480.6). MS-ES+ mass found: 480.22.

$^1$H-NMR (400 MHz, DMSO-$d_6$): δ [ppm]=1.14 (s, 3H), 1.40-1.55 (m, 1H), 1.70 (quin, 2H), 1.74-2.03 (m, 4H), 2.13-2.27 (m, 3H), 2.27-2.37 (m, 1H), 2.49-2.60 (m, 1H), 2.60-2.77 (m, 1H), 2.81-2.97 (m, 2H), 3.22 (q, 2H), 5.58-5.80 (m, 1H), 6.21-6.34 (m, 1H), 7.40 (d, 1H), 7.48-7.61 (m, 2H), 7.72 (dt, 1H), 8.36 (t, 1H), 8.45 (d, 1H), 8.50 (s, 1H), 12.0 (br. s., 1H).

EXAMPLE 26

N-{[17-(5-Fluoropyridin-3-yl)-15α-hydroxyestra-1,3,5(10),16-tetraen-3-yl]carbonyl}-N-methyl-β-alanine

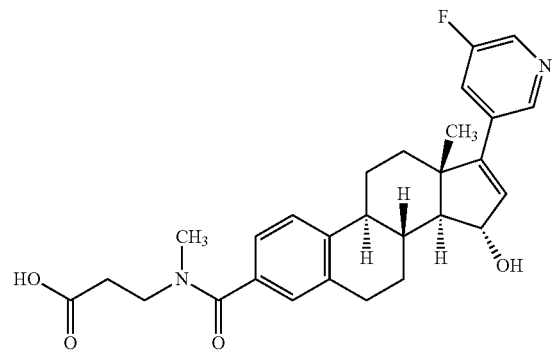

A 100 ml Erlenmeyer flask which contained 20 ml of an aqueous nutrient solution comprising 1% of maize steeping liquor and 1% of soybean meal (adjusted to pH 6.2) which had been sterilized in an autoclave at 121° C. for 20 minutes was inoculated with 0.2 ml of a DMSO/ice culture of the strain *Calonectria decora* (ATCC No. 14767) and shaken at 21° C. on a rotary shaker at 165 revolutions per minute for 48 hours. A 500 ml Erlenmeyer flask which had been charged with 100 ml of sterile medium of the same final composition as described for the preculture was inoculated with 8 ml of this preculture. This flask was shaken at 21° C. on a rotary shaker at 165 rotations per minute for 48 hours. Two 2 l Erlenmeyer flasks each containing 1 l of a sterile nutrient solution comprising 3% glucose monohydrate, 1% ammonium chloride, 0.2% sodium nitrate, 0.1% potassium dihydrogen phosphate, 0.2% dipotassium hydrogen phosphate, 0.05% potassium chloride, 0.05% magnesium sulphate heptahydrate and 0.002% iron(II) sulphate heptahydrate were inoculated with in each case 50 ml of this preculture. After a growth phase of 6 hours at 27° C. on a rotary shaker at 165 revolutions per minute at a temperature of 27° C., a solution of 50 mg of N-{[17-(5-fluoropyridin-3-yl)estra-1,3,5 (10),16-tetraen-3-yl]carbonyl}-N-methyl-β-alanine in 10 ml of DMF was divided into the two flasks. The flasks were shaken for a further 43 hours and then worked up. The two culture broths were combined and extracted with 1 l of isobutyl methyl ketone at 40 revolutions per minute in a 5 l glass extracting vessel for 19 hours. The organic phase was dried over sodium sulphate and concentrated to dryness. The residue was washed with methanol to remove the silicone oil. This gave 328 mg of a crude product. The crude product was absorbed on diatomaceous earth and chromatographed: method: Biotage Isolera, 10 g SNAP column, solvent: gradient from 2 to 20% methanol in ethyl acetate (1% of glacial acetic acid added). This gave 42 mg of the target compound.

HPLC Rt=4.8 min

HPLC conditions: A: water with 0.05% formic acid; B: acetonitrile with 0.1% formic acid; gradient: 0 min: 60:40 A/B; 12 min: 30:70 A/B; flow rate: 0.8 ml/min; column: Luna C18 (2) 5μ 125×4.6; detection wavelengths: 244 nm $^1$H-NMR (400 MHz, DMSO-d6): δ [ppm]=1.08 (s, 3H), 1.50-1.58 (m, 2H), 1.61-1.67 (m, 2H), 1.76-1.85 (m, 1H), 2.08-2.12 (m, 1H), 2.30-2.35 (m, 2H), 2.40-2.45 (m, 1H), 2.55 (2H superimposed by DMSO signal), 2.85-2.89 (m, 2H), 2.91 (s, 3H), 3.45 (br. s, 1H), 3.62 (br. s, 1H), 4.62 (d, 1H), 4.95 (br. s, 1H), 6.15 (s, 1H), 7.05 (s, 1H), 7.11 (d, 1H), 7.31 (d, 1H), 7.71 (d, 1H), 8.49 (d, 1H), 8.51 (s, 1H), 12.1 (br. s, 1H).

EXAMPLE 27

N-{[17-(5-Fluoropyridin-3-yl)-15β-hydroxyestra-1,3,5(10),16-tetraen-3-yl]carbonyl}-N-methyl-β-alanine

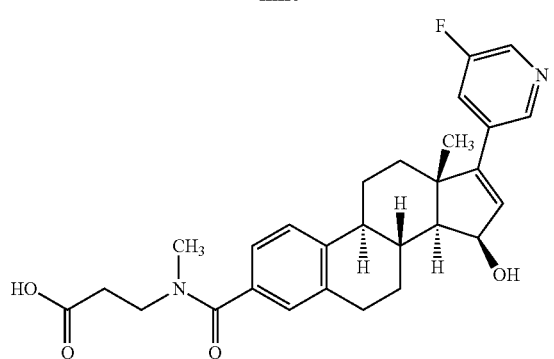

A 100 ml Erlenmeyer flask which contained 20 ml of an aqueous nutrient solution comprising 3% of glucose monohydrate, 1% maize steeping liquor, 0.2% sodium nitrate, 0.1% potassium dihydrogen phosphate, 0.2% dipotassium hydrogen phosphate, 0.05% potassium chloride, 0.05% magnesium sulphate heptahydrate and 0.002% iron(II) sulphate heptahydrate (adjusted to pH 6.0) which had been sterilized in an autoclave at 121° C. for 20 minutes was inoculated with 0.2 ml of a DMSO/ice culture of the strain *Mucor plumbeus* (CBS No. 29563) and shaken at 27° C. on a rotary shaker at 165 revolutions per minute for 65 hours. A 500 ml Erlenmeyer flask which had been charged with 100 ml of sterile medium of the same final composition as described for the preculture was inoculated with 8 ml of this preculture. This flask was shaken at 27° C. on a rotary shaker at 165 rotations per minute for 72 hours. Two 2 l Erlenmeyer flasks each containing 1 l of a sterile nutrient solution comprising 3% glucose monohydrate, 1% ammonium chloride, 0.2% sodium nitrate, 0.1% potassium dihydrogen phosphate, 0.2% dipotassium hydrogen phosphate, 0.05% potassium chloride, 0.05% magnesium sulphate heptahydrate and 0.002% iron(II) sulphate heptahydrate were inoculated with in each case 50 ml of this preculture. After a growth phase of 6 hours at 27° C. on a rotary shaker at 165 revolutions per minute at a temperature of 27° C., a solution of 50 mg of N-{[17-(5-fluoropyridin-3-yl)estra-1,3,5(10),16-tetraen-3-yl]carbonyl}-N-methyl-β-alanine in 10 ml of DMF was divided into the two flasks. The flasks were shaken for a further 43 hours and then worked up. The two culture broths were combined and extracted with 1 l of isobutyl methyl ketone at 40 revolutions per minute in a 5 l glass extracting vessel for 19 hours. The organic phase was dried over sodium sulphate and concentrated to dryness. The residue was washed with methanol to remove the silicone oil. This gave 236 mg of a crude product as a brown oil. The crude product was absorbed on diatomaceous earth and chromatographed: instrument: Biotage Isolera, 10 g SNAP column, solvent: gradient from 2 to 20% methanol in ethyl acetate (1% of glacial acetic acid added). This gave 35 mg of the target compound.

HPLC Rt=5.4 min

HPLC conditions: A: water with 0.05% formic acid; B: acetonitrile with 0.1% formic acid; gradient: 0 min: 60:40 A/B; 12 min: 30:70 A/B; flow rate: 0.8 ml/min; column: Luna C18 (2) 5μ 125×4.6;

Detection wavelengths: 244 nm $^1$H-NMR (400 MHz, DMSO-d6): δ [ppm]=1.28 (s, 3H); 1.38-1.60 (m, 4H); 1.69-1.78 (m, 1H); 2.01-2.08 (m, 1H); 2.20-2.28 (m, 1H); 2.30-2.40 (m, 1H); 2.55 (2H superimposed by DMSO signal); 2.85-2.90 (m, 5H); 3.10 (s, 1H); 3.45 (br. s, 1H); 3.57 (br. s, 1H); 4.50 (s, 1H); 4.69 (br. s, 1H); 6.30 (s, 1H); 7.05 (s, 1H); 7.08 (d, 1H); 7.28 (d, 1H); 7.71 (d7, 1H); 8.47 (d, 1H); 8.52 (s, 1H); 12.1 (br. s, 1H).

EXAMPLE 28

N-Methyl-N-{[17-(6-methylpyridazin-4-yl)estra-1,3,5(10),16-tetraen-3-yl]carbonyl}-β-alanine

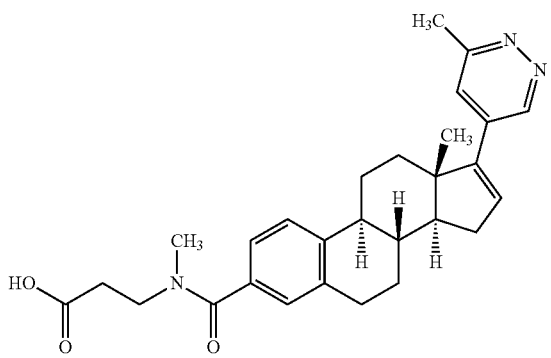

42 mg of 17-(6-methylpyridazin-4-yl)estra-1,3,5(10),16-tetraene-3-carboxylic acid (impure) and 36 mg of tert-butyl N-methyl-β-alaninate (2 equiv.) were dissolved in 2.5 ml of THF and 0.5 ml of DMF. 43 mg of 1-[3-(dimethylamino)propyl]-3-ethylcarbodiimide hydrochloride (EDC), 17 mg of 1-hydroxy-1H-benzotriazole hydrate and 0.047 ml of triethylamine were added, and the mixture was stirred at room temperature for 18 h. The reaction mixture was diluted with water and extracted three times with ethyl acetate. The combined organic phases were concentrated, 2 ml of dichloromethane and 0.5 ml of trifluoroacetic acid were added to the residue and the mixture was stirred at room temperature for 6 h. The mixture was concentrated and the product was purified by preparative HPLC. This gave 18 mg of the title compound.

$C_{28}H_{33}N_3O_3$ (459.59). MS-ES+ mass found: 459.25.

$^1$H-NMR (400 MHz, DMSO-d6): δ [ppm]=1.02 (s, 3H), 1.35-1.77 (m, 5H), 1.84-1.95 (m, 1H), 2.07-2.42 (m, 6H), 2.58 (s, 3H), 2.78-2.95 (m, 5H), 3.41 (br. s), 3.57 (br. s), 6.54-6.59 (m, 1H), 7.02-7.13 (m, 2H), 7.29 (d, 1H), 7.49 (d, 1H), 9.10 (d, 1H), 12.3 (br. s, 1H).

EXAMPLE 29

N-Methyl-N-{[17-(pyridin-3-yl)estra-1,3,5(10),16-tetraen-3-yl]carbonyl}-β-alanine

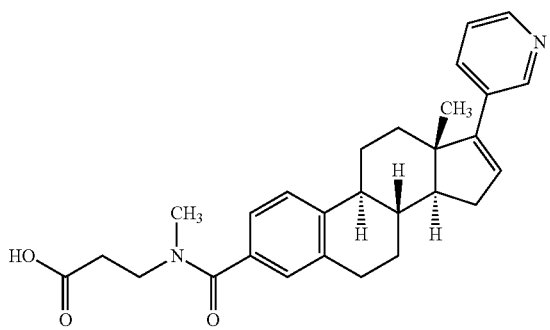

100 mg of 17-(pyridin-3-yl)estra-1,3,5(10),16-tetraene-3-carboxylic acid and 89 mg of tert-butyl N-methyl-β-alaninate (2 equiv.) were dissolved in 3 ml of THF and 0.5 ml of DMF. 107 mg of 1-[3-(dimethylamino)propyl]-3-ethylcarbodiimide hydrochloride (EDC), 43 mg of 1-hydroxy-1H-benzotriazole hydrate and 0.116 ml of triethylamine were added, and the mixture was stirred at room temperature for 18 h. The reaction mixture was diluted with water and extracted three times with ethyl acetate. The combined organic phases were concentrated, 3 ml of dichloromethane and 1 ml of trifluoroacetic acid were added to the residue and the mixture was stirred at room temperature for 20 h. The mixture was concentrated and the product was purified by preparative HPLC. This gave 78 mg of the title compound.

$C_{28}H_{32}N_2O_3$ (444.58). MS-ES+ mass found: 444.24.

$^1$H-NMR (400 MHz, DMSO-$d_6$): δ [ppm]=0.99 (s, 3H), 1.37-1.67 (m, 4H), 1.73 (td, 1H), 1.86-1.94 (m, 1H), 2.06-2.17 (m, 2H), 2.24-2.45 (m, 3H), 2.80-2.93 (m, 5H), 3.42 (br. s.), 3.57 (br. s.), 6.12 (dd, 1H), 7.02-7.11 (m, 2H), 7.26-7.35 (m, 2H), 7.77 (dt, 1H), 8.42 (dd, 1H), 8.59 (d, 1H), 12-3 (br. s., 1H).

EXAMPLE 30

4-({[17-(5-Methoxypyridin-3-yl)estra-1,3,5(10),16-tetraen-3-yl]carbonyl}amino)butanoic acid

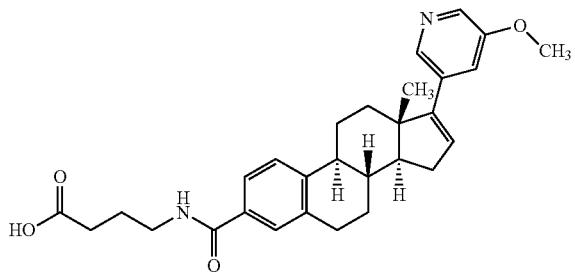

Analogously to Example 1, 100 mg (0.26 mmol) of 17-(5-methoxypyridin-3-yl)estra-1,3,5(10),16-tetraene-3-carboxylic acid and 79 mg of methyl 4-aminobutanoate hydrochloride were converted into 64 mg (53% of theory) of the title compound.

$C_{29}H_{34}N_2O_4$ (474.61). MS-ES+ mass found: 474.25.

$^1$H-NMR (300 MHz, DMSO-$d_6$): δ [ppm]=0.99 (s, 3H), 1.38-1.78 (m, 7H), 1.86-1.96 (m, 1H), 2.04-2.43 (m, 7H), 2.83-2.92 (m, 2H), 3.15-3.26 (m, 2H), 3.81 (s, 3H), 6.16 (s, 1H), 7.23-7.34 (m, 2H), 7.51-7.59 (m, 2H), 8.16 (d, 1H), 8.20 (d, 1H), 8.33 (t, 1H), 12.0 (br. s., 1H).

Pharmacological Examination of the Compounds According to the Invention In Vitro

EXAMPLE 31

AKR1C3-Inhibitory Activity

The AKR1C3-inhibitory activity of the substances of the present invention was measured in the AKR1C3 assay described in the paragraphs below.

Essentially, the enzyme activity is measured by quantification of the Coumberol from Coumberone (Halim, M., Yee, D. J., and Sames, D., J. AM. CHEM. SOC. 130, 14123-14128 (2008) and Yee, D. J., Balsanek, V., Bauman, D. R., Penning, T. M., and Sames, D., Proc. Natl. Acad. Sci. USA 103, 13304-13309 (2006)). In this test, the increase of the highly fluorescent Coumberol by NADPH—(nicotinamide adenine dinucleotide phosphate)-dependent reduction of the non-fluorescent Coumberone by AKR1C3 can be determined.

The enzyme used was recombinant human AKR1C3 (Aldo-keto reductase family 1 member C3) (GenBank Accession No. NM_003739). This was expressed in *E. coli* as GST (glutathione S transferase) fusion protein and purified by glutathione Sepharose affinity chromatography. The GST was removed by digestion with thrombin and subsequent size exclusion chromatography (Dufort, I., Rheault, P., Huang, X F., Soucy, P., and Luu-The, V., Endocrinology 140, 568-574 (1999)).

For the assay, 50 nl of a 100-fold concentrated solution of the test substance in DMSO were pipetted into a black low-volume 384-well microtiter plate (Greiner Bio-One, Frickenhausen, Germany), 2.0 µl of a solution of AKR1C3 in assay buffer [50 mM potassium phosphate buffer pH 7, 1 mM DTT, 0.0022% (w/v) Pluronic F-127, 0.01% BSA (w/v) and protease inhibitor cocktail (Complete, EDTA-free Protease Inhibitor Cocktail from Roche)] were added and the mixture was incubated for 15 min to allow pre-binding of the substances to the enzyme prior to the enzyme reaction. The enzyme reaction was then started by addition of 3 µl of a solution of NADPH (16.7 µM→final concentration in 5 µl of assay volume is 10 µM) and Coumberone (0.5 µM→final concentration in 5 µl of assay volume is 0.3 µM) in assay buffer, and the resulting mixture was incubated at 22° C. for the reaction time of 90 min. The concentration of the AKR1C3 was adapted to the respective activity of the enzyme preparation and adjusted such that the assay was carried out in the linear range. Typical concentrations were in the region of 1 nM. The reaction was stopped by addition of 5 µl of a stop solution consisting of the inhibitor EM-1404 [F. Labrie et al. U.S. Pat. No. 6,541,463, 2003] (2 µM→final concentration in 5 µl of assay volume is 1 µM). The fluorescence of the Coumberole was then measured at 520 nm (excitation at 380 nm) using a suitable measuring instrument (Pherastar from BMG Labtechnologies). The intensity of the fluorescence was used as a measure of the amount of Coumberole formed and thus of the enzyme activity of AKR1C3. The data were normalized (enzyme reaction without inhibitor=0% inhibition; all other assay components, but no enzyme=100% inhibition). Usually, the test substances were tested on the same microtiter plate at 11 different concentrations in the range from 20 µM to 96.8 pM (20 µM, 5.9 µM, 1.7 µM, 0.5 µM, 0.15 µM, 44 nM, 12.9 nM, 3.8 nM, 1.1 nM, 0.3 nM and 96.8 pM, the dilution series were prepared prior to the assay on the level of the 100-fold concentrated solution by serial 1:3 dilutions with 100% DMSO) in double for each concentration, and the $IC_{50}$ values were calculated using a 4-parameter fit.

As described, the pharmacological substances claimed were examined for their inhibitory activity on the AKR1C3 enzyme (see Table 1). For the major part of the range of structures claimed, these compounds show a strong inhibition of AKR1C3 in vitro ($IC_{50}$ values <50 nM) and in most cases even $IC_{50}$ values <20 nM.

TABLE 1

Inhibition of AKR1C3 of the compounds according to the invention (for the major part of the compounds, the values of two experimental determinations are stated)

| Exemplary compound | AKR1C3 enzyme inhibition $IC_{50}$ [nmol/l]) | Exemplary compound | AKR1C3 enzyme inhibition $IC_{50}$ [nmol/l]) | Exemplary compound | AKR1C3 enzyme inhibition $IC_{50}$ [nmol/l]) |
|---|---|---|---|---|---|
| 1 | 1.4 | 9 | 8.9 | 19 | 17.8 |
| 1 | 1.9 | 10 | 7.3 | 19 | 26.7 |
| 2 | 1.3 | 10 | 4.9 | 20 | 45.5 |
| 2 | 1.4 | 11 | 2.2 | 20 | 46.3 |
| 3 | 9.2 | 11 | 1.8 | 21 | 8.5 |
| 3 | 10.2 | 12 | 1.2 | 22 | 4.2 |
| 4 | 13.9 | 12 | 1.7 | 23 | 1.9 |
| 4 | 8.9 | 13 | 0.8 | 24 | 5.3 |
| 5 | 9.1 | 13 | 1.8 | 25 | 29.1 |
| 5 | 8.0 | 14 | 9.8 | 25 | 16.8 |
| 5 | 4.3 | 14 | 17.9 | 26 | 11.0 |
| 5 | 3.6 | 15 | 6.9 | 26 | 16.6 |
| 6 | 21.1 | 15 | 7.2 | 27 | 35.3 |
| 6 | 21.0 | 16 | 4.4 | 27 | 24.2 |
| 7 | 8.5 | 16 | 6.9 | 28 | 0.5 |
| 7 | 9.6 | 17 | 29.7 | 29 | 2.5 |
| 8 | 8.5 | 17 | 37.6 | 30 | 7.3 |
| 8 | 6.8 | 18 | 23.5 | 30 | 11.2 |
| 9 | 8.3 | 18 | 31.8 | | |
| 9 | 8.9 | 19 | 26.7 | | |

EXAMPLE 32

Inhibition of Cyp17A1

CYP17A1 (synonym 17α-hydroxylase/17.20-lyase) is an enzyme which adds a hydroxyl group to position 17 of the steroidal D ring of pregnenolone and progesterone, thus forming 17α-hydroxyprogesterone and 17α-hydroxypregnenolone. Subsequently, dehydroepiandro-sterone and androstendione are formed. The known CYP17A1 inhibitor abiraterone, for example, is used for the therapy of metastased, castration-refractory prostate carcinoma after failure of a docetaxel-based chemotherapy (Urologe 2010, 49, 64-68). Abiraterone blocks the androgen synthesis and oestrogen synthesis in the entire body and thus lowers the hormone production in a non-tissue-specific manner, which leads to unwanted side-effects (cf. press release of the FDA, U.S. Food and Drug Admistration dated 28 Apr. 2011).

Surprisingly, it has been found that the compounds according to the invention inhibit CYP17A1 only very weakly, if at all, although they have an aromatic nitrogen-containing heterocycle in position 17 of the steroidal skeleton.

Assay Description:

The inhibition of CYP17A1 by the test compounds was evaluated using a recombinant enzyme. Human CYP17A1 was expressed in E. coli (Ehmer, P. B. et al.; J. Steroid Biochem. Mol. Biol., 75, 57-63 (2000)). The microsomal fraction and 140 µL of phosphate buffer (50 mM Na phosphate, 1 mM $MgCl_2$, 0.1 mM EDTA, 0.1 mM dithiothreitol, pH 7.4) were preincubated separately with a mixture of progesterone (24.95 µM) and $^3$H-progesterone (0.05 µM, 101.3 Ci/mmol), 50 µM of an NADPH regeneration system (in phosphate buffer with 10 mM NADP+, 100 mM glucose 6-phosphate and 2.5 U of glucose 6-phosphate dehydrogenase) and the appropriate test substances (in 5 µl of DMSO) at 37° C. for 5 minutes. The reaction was started by addition of the enzyme and, after 30 minutes of incubation at 37° C., stopped by addition of 50 µl of 1N hydrochloric acid.

The steroids were extracted with ethyl acetate. After evaporation of the organic phase, the steroids were taken up in acetonitrile. 16α-Hydroxyprogesterone, 17α-hydroxyprogesterone and progesterone were separated using acetonitrile/water (45:55) as mobile phase on a C18 reverse-phase chromatography column (Nucleodur C18 Gravity, 3 µm, Macherey-Nagel, Düren, Germany) on an HPLC system (Agilent 1100 Series, Agilent Technologies, Waldbronn, Germany). Detection and quantification of the steroids was carried out using a radio flow detector (Berthold Technologies, Bad Wildbad, Germany). The inhibition was calculated using the formula below:

$$\% \text{ inhibition} = \frac{(\%(17\alpha-\text{hydroxyprogesterone} + 16\alpha-\text{hydroxyprogesterone})}{\%(17\alpha-\text{hydroxyprogesterone} + 16\alpha-\text{hydroxyprogesterone} + progesterosterone)} \cdot 100$$

Each value was calculated from at least three independent experiments. The final $IC_{50}$ value was calculated as the mean of 3 or 4 independent $IC_{50}$ values.

The compounds according to the invention show no or an only very weakly pronounced inhibition of CYP17A1 (Table 2) with IC$_{50}$ values of more than 10 µM compared to the known CYP17A1 inhibitor abiraterone (employed as free base).

TABLE 2

Inhibition of human CYP17

| Exemplary compound | IC$_{50}$ ± SD (µM) CYP17 |
| --- | --- |
| Abiraterone | 0.029 ± 0.004 |
| 5 | 85.5 ± 7.7 |
| 2 | ~200 (49%)[a] |
| 9 | No inhibition |
| 10 | 15.19 ± 1.58 |

[a] % Inhibition at a concentration of 200 µM substance

EXAMPLE 33

Solubility in Aqueous Buffer pH 6.5

Determination of the Thermodynamic Solubility in Aqueous Buffer pH 6.5 (Shake-Flask Method)

The thermodynamic solubility was determined according to the shake-flask method [literature: Edward H. Kerns and Li Di (2008) Solubility Methods in: Drug-like Properties: Concepts, Structure Design and Methods, p 276-286. Burlington, Mass., Academic Press].

Here, a saturated solution of the active compound in buffer pH 6.5 was prepared and stirred for 24 h to ensure that an equilibrium between the solid and the substance in solution had formed. The solution was then centrifuged, and the concentration of the solution obtained was quantified with the aid of a calibration line.

For the sample, 2 mg of solid substance were weighed out accurately into a 4 ml glass bottle. 1 ml of phosphate buffer pH 6.5 was added. This solution was stirred on a stirrer at room temperature for 24 h. The solution was then centrifuged. To prepare the comparison for the calibration, 2 mg of solid substance were weighed out accurately and dissolved in 30 ml of acetonitrile. After a short ultrasound treatment, the solution was diluted with water to 50 ml.

Sample and comparison were quantified using HPLC with UV detection. Each sample was injected three times per injection volume (5 and 50 µl). For the comparison, three injection volumes (5 µl, 10 µl and 20 µl) were injected.

The following chromatography conditions were chosen:
HPLC column: Xterra MS C18 2.5 µm 4.6×30 mm
Injection volumes: sample: 3×5 µl and 3×50 µl
  comparison: 5 µl, 10 µl, 20 µl
Flow rate: 1.5 ml/min
Mobile phase: acidic gradient:
  A: water/0.01% trifluoroacetic acid (TFA)
  B: acetonitrile/0.01% TFA
  0 min→95% A 5% B
  0-3 min→35% A 65% B, linear gradient
  3-5 min→35% A 65% B, isocratic
  5-6 min→95% A 5% B, isocratic
UV detector: a wavelength close to the absorption maximum (between 200 and 400 nm)

The areas of the sample and comparison injections and the calculation of the solubility (in mg/l) were determined using the HPLC software (Waters Empower 2 FR).

For the compound according to the invention Example 2, a solubility of 354 mg/l was measured; the known AKR1C3 inhibitor EM-1404 showed a solubility of 0.1 mg/l.

EXAMPLE 34

Endometriosis Model

To examine the in vivo efficacy of the exemplary compound Example 2, an endometriosis model in common marmosets was used. 4-8 year old female common marmosets were employed (body weight between 340 and 460 g). In these animals, endometriosis was induced by puncturing the uterus during a laparotomy and rinsing with sterile medium such that uterine cells entered the abdomen via the upper ducts [Einspanier et al., MolHum Reprod 2006]. The procedure is repeated after 3 months. Prior to the actual start of the treatment, the animals are subjected to a laparotomy and examined for the presence of endometriotic lesions on the bladder, the uterus and the ovaries. 6 weeks later, the treatment was started. Two treatment groups were employed, with a group size of n=6 animals per group. Group 1 was treated with vehicle (strawberry/banana juice) only, group 2 was treated with the test substance administered in the vehicle. 30 mg/kg of the test substance were administered orally once per day. The treatment period was 6 weeks. Immediately after the end of the treatment, a 2$^{nd}$ laparoscopy was carried out and the number and size of the lesions on uterus, ovaries and bladder was determined again. Since both prior to and after the treatment, hardly any lesions were found on the ovaries, the ovaries as type of lesion was not taken into account during the evaluation.

The invention claimed is:
1. Compounds of the formula (I)

in which
R1 and R2
independently of one another represent hydrogen, fluorine, chlorine, nitrile, trifluoromethyl, pentafluoroethyl, methoxy, ethoxy, trifluoromethoxy, —OCH$_2$CF$_3$, CH$_3$SO$_2$—, CH$_3$CH$_2$SO$_2$—, —(C=O)CH$_3$, carboxyl, C$_1$-C$_4$-alkyl, hydroxy, —CH$_2$OH, —C(CH$_3$)$_2$OH, —CONH$_2$, —(C=O)NH-alkyl, —(C=O)N(CH$_3$)$_2$, —SO$_2$NH$_2$, —SO$_2$NH(CH$_3$), —SO$_2$N(CH$_3$)$_2$ or the replacement of a C—H group in the pyridine ring by a nitrogen atom and R3 and R4
  represent hydrogen or
  R3 represents hydroxy, fluorine, methoxy or ethoxy and R4 represents hydrogen or
  R3 represents hydrogen and R4 represents hydroxy, fluorine, methoxy or ethoxy and
R5 and R6
  represent hydrogen or
  R5 represents fluorine, hydroxy, methoxy or ethoxy and R6 represents hydrogen or
  R5 represents hydrogen and R6 represents fluorine and
R7
  represents hydrogen, $C_1$-$C_4$-alkyl, $C_3$-$C_6$-cycloalkyl, cyclopropylmethyl, trifluoromethyl or 2,2,2-trifluoroethyl and
R8
  represents —$CR^aR^b$—COOH where
    $R^a$ and $R^b$ independently of one another represent hydrogen, methyl, ethyl or
    $R^a$ and $R^b$ together represent —$(CH_2)_n$— where n=2, 3, 4 or 5, where up to 4 hydrogen atoms of the $CH_2$ groups may be replaced by fluorine atoms or
    $R^a$ and $R^b$ together represent —$CH_2$—O—$CH_2$—, —$CH_2$—NH—$CH_2$—, —$CH_2$—N($CH_3$)—$CH_2$—, —$CH_2CH_2$—O—$CH_2CH_2$—, —$CH_2CH_2$—NH—$CH_2CH_2$—, —$CH_2CH_2$—N($CH_3$)—$CH_2CH_2$— or
    $R^a$ represents hydrogen, methyl or ethyl and $R^b$ together with R7 represents —$(CH_2)n^1$— where $n^1$=1, 2, 3, 4, where up to 4 hydrogen atoms of the $CH_2$ groups may be replaced by fluorine atoms or
    $R^a$ together with R7 represents —$CH_2$—O—$CH_2CH_2$—, —$CH_2$—N($CH_3$)—$CH_2CH_2$— and $R^b$ represents hydrogen, methyl or ethyl or
  represents —$CR^cR^d$—$CR^eR^f$—COOH where
    $R^c$, $R^d$, $R^e$, $R^f$ represent hydrogen or
    $R^c$, $R^d$ independently of one another represent methyl, ethyl or together represent —$(CH_2)_n$— where n=2, 3, 4, 5 or —$CH_2CH_2$—O—$CH_2CH_2$— and $R^e$, $R^f$ represent hydrogen or
    $R^c$, $R^d$ represent hydrogen and $R^e$, $R^f$ independently of one another represent methyl, ethyl or together represent —$(CH_2)n$— where n=2, 3, 4, 5, —$CH_2CH_2$—O—$CH_2CH_2$—, —$CH_2CH_2$—NH—$CH_2CH_2$—, —$CH_2CH_2$—N($CH_3$)—$CH_2CH_2$— or —$CH_2$—O—$CH_2$— or
    $R^c$ represents methyl, ethyl, trifluoromethyl and $R^d$, $R^e$ and $R^f$ represent hydrogen or
    $R^c$, $R^d$ and $R^f$ represent hydrogen and $R^e$ represents methyl, ethyl, trifluoromethyl, hydroxy or methoxy or
    $R^c$ and $R^e$ together represent —$(CH_2)n^1$— where $n^1$=1, 2, 3 or 4 and $R^d$ and $R^f$ represent hydrogen or
  represents —$CH_2$—$CH_2$—$CHR^g$—COOH where
    $R^g$ represents hydrogen or
    $R^g$ and R7 together represent —$CH_2$—$CH_2CH_2$—
and their salts.

2. Compounds according to claim 1 of the formula (II) and the formula (III)

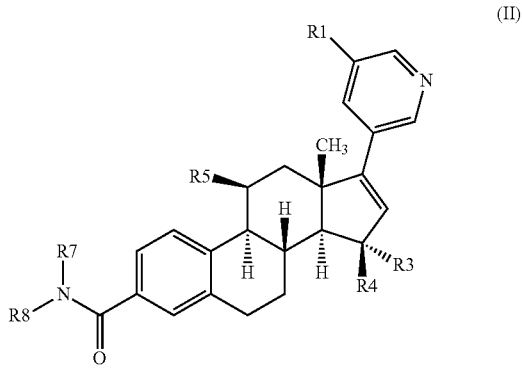

(II)

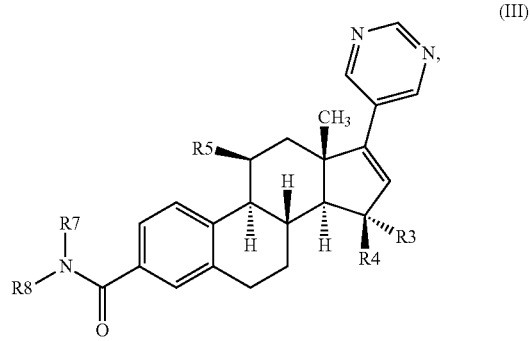

(III)

in which
R1
  represents hydrogen, fluorine, chlorine, nitrile, methoxy, ethoxy, trifluoromethoxy, methyl, ethyl, trifluoromethyl, —(C=O)$CH_3$ and
R3 and R4
  represent hydrogen or
  R3 represents hydroxy and R4 represents hydrogen or
  R3 represents hydrogen and R4 represents hydroxy and
R5
  represents hydrogen or fluorine and
R7
  represents hydrogen or $C_1$-$C_4$-alkyl and
R8
  represents —$CR^aR^b$—COOH where
    $R^a$ and $R^b$ independently of one another represent hydrogen, methyl or ethyl or
    $R^a$ and $R^b$ together represent —$(CH_2)_n$— where n=2, 3, 4 or 5 or
    $R^a$ represents hydrogen and $R^b$ together with R7 represents —$(CH_2)n^2$— where $n^2$=3 or 4 or
  represents —$CR^cR^d$—$CR^eR^f$—COOH where
    $R^c$, $R^d$, $R^e$, $R^f$ represent hydrogen or
    $R^c$, $R^d$ represent hydrogen and $R^e$, $R^f$ independently of one another represent methyl, ethyl or together represent —$(CH_2)n$- where n=2, 3, 4, 5 or —$CH_2CH_2$—O—$CH_2CH_2$— or
    $R^c$ represents methyl or ethyl and $R^d$, $R^e$ and $R^f$ represent hydrogen or
    $R^c$ and $R^e$ together represent —$(CH_2)n^1$— where $n^1$=1, 2, 3 or 4 and $R^d$ and $R^f$ represent hydrogen or
  represents —$CH_2$—$CH_2$—$CHR^g$—COOH where
    $R^g$ represents hydrogen or
    $R^g$ and R7 together represent —$CH_2CH_2$—
and their salts.

3. Compounds according to claim 1, in which
R1
  represents hydrogen, fluorine, chlorine, nitrile, methoxy, trifluoromethyl and
R3 and R4
  represent hydrogen or
  R3 represents hydroxy and R4 represents hydrogen or
  R3 represents hydrogen and R4 represents hydroxy and
R5
  represents hydrogen or fluorine and
R7
  represents hydrogen, methyl or ethyl and
R8
  represents —$CR^aR^b$—COOH where
    $R^a$ and $R^b$ independently of one another represent hydrogen, methyl or ethyl or
    $R^a$ represents hydrogen and $R^b$ together with R7 represents —$(CH_2)n^2$— where $n^2$=3 or 4 or
  represents —$CR^cR^d$—$CR^eR^f$—COOH where
    $R^c$, $R^d$, $R^e$, $R^f$ represent hydrogen or
    $R^c$, $R^d$ represent hydrogen and $R^e$, $R^f$ independently of one another represent methyl or ethyl or together represent —$(CH_2)n^3$— where $n^3$=2, 4, 5 or represent —$CH_2CH_2$—O—$CH_2CH_2$— or
    $R^c$ represents methyl and $R^d$, $R^e$ and $R^f$ represent hydrogen or
    $R^c$ and $R^e$ together represent —$(CH_2)n^2$— where $n^2$=3 or 4 and $R^d$ and $R^f$ represent hydrogen or
  represents —$CH_2$—$CH_2$—$CHR^g$—COOH where
    $R^g$ represents hydrogen or
    $R^g$ and R7 together represent —$CH_2CH_2$—
and their salts.

4. Compounds according to claim 1, in which
R1
  represents hydrogen, fluorine, methoxy, trifluoromethyl and
R3 and R4
  represent hydrogen or
  R3 represents hydroxy and R4 represents hydrogen or
  R3 represents hydrogen and R4 represents hydroxy and
R5
  represents hydrogen or fluorine and
R7
  represents hydrogen or methyl and
R8
  represents —$CR^aR^b$—COOH where
    $R^a$ and $R^b$ independently of one another represent hydrogen or methyl or
    $R^a$ represents hydrogen and $R^b$ together with R7 represents —$(CH_2)_3$— or
  represents —$CR^cR^d$—$CR^eR^f$—COOH where
    $R^c$, $R^d$, $R^e$, $R^f$ represent hydrogen or
    $R^c$ and $R^d$ represent hydrogen and $R^e$ and $R^f$ represent methyl or together represent —$(CH_2)n^2$— where $n^2$=2 or 4 or represent —$CH_2CH_2$—O—$CH_2CH_2$— or
    $R^c$ represents methyl and $R^d$, $R^e$ and $R^f$ represent hydrogen or
    $R^c$ and $R^e$ together represent —$(CH_2)_3$— and $R^d$ and $R^f$ represent hydrogen or
  represents —$CH_2$—$CH_2$—$CHR^g$—COOH where
    $R^g$ represents hydrogen or
    $R^g$ and R7 represent —$CH_2CH_2$—
and their salts.

5. A Compound according to claim 1 that is
4-[({[17-(5-fluoropyridin-3-yl)estra-1,3,5(10),16-tetraen-3-yl]carbonyl}amino)-methyl]-3,4,5,6-tetrahydro-2H-pyran-4-carboxylic acid
N-{[17-(5-fluoropyridin-3-yl)estra-1,3,5(10),16-tetraen-3-yl]carbonyl}-N-methyl-β-alanine
1-[({[17-(5-fluoropyridin-3-yl)estra-1,3,5(10),16-tetraen-3-yl]carbonyl}amino)-methyl]cyclopropan-1-carboxylic acid
1-[({[17-(5-fluoropyridin-3-yl)estra-1,3,5(10),16-tetraen-3-yl]carbonyl}amino)-methyl]cyclopentane-1-carboxylic acid
3-({[17-(5-fluoropyridin-3-yl)estra-1,3,5(10),16-tetraen-3-yl]carbonyl}amino)-2,2-dimethylpropanoic acid
1-{[17-(5-fluoropyridin-3-yl)estra-1,3,5(10),16-tetraen-3-yl]carbonyl}piperidine-4-carboxylic acid
N-{[17-(5-fluoropyridin-3-yl)estra-1,3,5(10),16-tetraen-3-yl]carbonyl}-2-methylalanine
4-({[17-(5-fluoropyridin-3-yl)estra-1,3,5(10),16-tetraen-3-yl]carbonyl}amino)butanoic acid
N-{[17-(5-fluoropyridin-3-yl)estra-1,3,5(10),16-tetraen-3-yl]carbonyl}-β-alanine
N-{[17-(5-fluoropyridin-3-yl)estra-1,3,5(10),16-tetraen-3-yl]carbonyl}glycine
(1R*,2S*)-2-({[17-(5-fluoropyridin-3-yl)estra-1,3,5(10),16-tetraen-3-yl]carbonyl}-amino)cyclopentane-1-carboxylic acid
(S)-3-({[17-(5-fluoropyridin-3-yl)estra-1,3,5(10),16-tetraen-3-yl]carbonyl}amino)-butanoic acid
(R)-3-({[17-(5-fluoropyridin-3-yl)estra-1,3,5(10),16-tetraen-3-yl]carbonyl}amino)-butanoic acid
3-({[17-(5-methoxypyridin-3-yl)estra-1,3,5(10),16-tetraen-3-yl]carbonyl}amino)-2,2-dimethylpropanoic acid
N-{[17-(5-methoxypyridin-3-yl)estra-1,3,5(10),16-tetraen-3-yl]carbonyl}-β-alanine
N-{[17-(5-methoxypyridin-3-yl)estra-1,3,5(10),16-tetraen-3-yl]carbonyl}-N-methyl-β-alanine
N-{[17-(pyrimidin-5-yl)estra-1,3,5(10),16-tetraen-3-yl]carbonyl}-β-alanine
4-({[17-(pyrimidin-5-yl)estra-1,3,5(10),16-tetraen-3-yl]carbonyl}amino)butanoic acid
N-methyl-N-{[17-(pyrimidin-5-yl)estra-1,3,5(10),16-tetraen-3-yl]carbonyl}-β-alanine
2,2-dimethyl-3-({[17-(pyrimidin-5-yl)estra-1,3,5(10),16-tetraen-3-yl]carbonyl}-amino)propanoic acid
N-({17-[5-(trifluoromethyl)pyridin-3-yl]estra-1,3,5(10),16-tetraen-3-yl}carbonyl)-β-alanine
N-methyl-N-({17-[5-(trifluoromethyl)pyridin-3-yl]estra-1,3,5(10),16-tetraen-3-yl}-carbonyl)-β-alanine
N-{[17-(5-fluoropyridin-3-yl)estra-1,3,5(10),16-tetraen-3-yl]carbonyl}-L-proline
N-{[17-(5-fluoropyridin-3-yl)estra-1,3,5(10),16-tetraen-3-yl]carbonyl}-D-proline
4-({[11β-fluoro-17-(5-fluoropyridin-3-yl)estra-1,3,5(10),16-tetraen-3-yl]carbonyl}-amino)butanoic acid
N-{[17-(5-fluoropyridin-3-yl)-15α-hydroxyestra-1,3,5(10),16-tetraen-3-yl]carbonyl}-N-methyl-β-alanine
N-{[17-(5-fluoropyridin-3-yl)-15β-hydroxyestra-1,3,5(10),16-tetraen-3-yl]carbonyl}-N-methyl-β-alanine
N-methyl-N-{[17-(6-methylpyridazin-4-yl)estra-1,3,5(10),16-tetraen-3-yl]carbonyl}-β-alanine
N-methyl-N-{[17-(3-pyridin-3-yl)estra-1,3,5(10),16-tetraen-3-yl]carbonyl}-β-alanine
4-({[17-(5-methoxypyridin-3-yl)estra-1,3,5(10),16-tetraen-3-yl]carbonyl}amino)-butanoic acid
and their salts.

6. A pharmaceutical composition comprising a compound of claim 1 and at least one active compound selected from the group consisting of selective oestrogen receptor modulators (SERMs), oestrogen receptor (ER) antagonists, aromatase inhibitors, 17β HSD1 inhibitors, steroid sulphatase (STS) inhibitors, GnRH agonists and antagonists, kisspeptin receptor (KISSR) antagonists, selective androgen receptor modulators (SARMs), androgens, 5α-reductase inhibitors, selective progesterone receptor modulators (SPRMs), gestagens, antigestagens, oral contraceptives, inhibitors of mitogen activating protein (MAP) kinases and inhibitors of the MAP kinases kinases (Mkk3/6, Mek1/2, Erk1/2), inhibitors of the protein kinases B (PKBα/β/γ; Akt1/2/3), inhibitors of the phosphoinositide 3-kinases (PI3K), inhibitors of the cyclin-dependent kinase (CDK1/2), inhibitors of the hypoxia-induced signal path (HIF1alpha inhibitors, activators of prolyl hydroxylases), histone deacetylase (HDAC) inhibitors, prostaglandin F receptor (FP) (PTGFR) antagonists and non-steroidal antiflammatory drugs (NSAIDs).

7. A composition comprising a compound according to claim 1 in combination with a pharmaceutically acceptable excipient.

8. A Method for treating endometriosis, uterine leiomyomas, uterine bleeding disorders, dysmenorrhoea, prostate carcinoma, prostate hyperplasia, acne, seborrhoea, hair loss, premature sexual maturity, polycystic ovary syndrome, breast cancer, lung cancer, endometrial carcinoma, renal cell carcinoma, bladder carcinoma, non-Hodgkin lymphomas, chronic obstructive pulmonary disease (COPD), adiposity, or inflammatory pain comprising the step of administering to a patient in need thereof a compound according to claim 1.

* * * * *